(12) United States Patent
Foelsch et al.

(10) Patent No.: US 12,354,739 B2
(45) Date of Patent: Jul. 8, 2025

(54) BEACON-BASED SYSTEMS AND METHODS FOR COMMUNICATIVELY PAIRING A DEVICE WITH A MEDICAL SYSTEM

(71) Applicant: Intuitive Surgical Operations, Inc., Sunnyvale, CA (US)

(72) Inventors: Boris Foelsch, Palo Alto, CA (US); Mahdi Azizian, San Jose, CA (US); Alan S Bradley, Alameda, CA (US); Christopher R. Burns, San Jose, CA (US); Liron Leist, San Jose, CA (US); A. Jonathan McLeod, Sunnyvale, CA (US); Wen Pei Liu, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 447 days.

(21) Appl. No.: 17/777,520

(22) PCT Filed: Nov. 24, 2020

(86) PCT No.: PCT/US2020/062065
§ 371 (c)(1),
(2) Date: May 17, 2022

(87) PCT Pub. No.: WO2021/108437
PCT Pub. Date: Jun. 3, 2021

(65) Prior Publication Data
US 2023/0057639 A1     Feb. 23, 2023

Related U.S. Application Data

(60) Provisional application No. 62/940,794, filed on Nov. 26, 2019, provisional application No. 62/940,792, filed on Nov. 26, 2019.

(51) Int. Cl.
*G16H 40/63* (2018.01)
*G16H 40/20* (2018.01)
*H04W 12/50* (2021.01)

(52) U.S. Cl.
CPC ............ *G16H 40/63* (2018.01); *G16H 40/20* (2018.01); *H04W 12/50* (2021.01)

(58) Field of Classification Search
None
See application file for complete search history.

(56) References Cited

U.S. PATENT DOCUMENTS 8,360,975 B1    1/2013   Schwieterman et al.
2013/0106977 A1   5/2013   Chu et al.
(Continued)

OTHER PUBLICATIONS

Carotenuto et al. ("An Indoor Ultrasonic System for Autonomous 3-D Positioning," in IEEE Transactions on Instrumentation and Measurement, vol. 68, No. 7, pp. 2507-2518, Jul. 2019) (Year: 2019).*

(Continued)

*Primary Examiner* — Christopher B Tokarczyk

(57) ABSTRACT

A device pairing system is configured to determine that an auxiliary device detects an ultrasonic beacon emitted by a beacon generator and identify, in response to the determination that the auxiliary device detects the ultrasonic beacon, a medical system associated with the ultrasonic beacon. The auxiliary device is further configured to communicatively pair, in response to the identification of the medical system, the auxiliary device with the identified medical system.

20 Claims, 19 Drawing Sheets

(56) References Cited

U.S. PATENT DOCUMENTS

2019/0201122 A1* 7/2019 Shelton, IV ........... A61B 34/10
2019/0327161 A1* 10/2019 Cannell ............... H04L 43/0817

OTHER PUBLICATIONS

International Search Report and Written Opinion for Application No. PCT/US2020/062065, mailed Apr. 8, 2021, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2020/62065, mailed Jun. 9, 2022, 9 pages.

* cited by examiner

900 ↘

| Location ID | Medical System ID | Beacon Generator ID | Surgical Session ID |
|---|---|---|---|
| OR001 | DV001 | BG001 | PATIENT_A |
| OR002 | DV002 | BG002 | PATIENT_B |
| OR002 | DV002 | BG003 | PATIENT_B |
| OR002 | DV002 | BG004 | PATIENT_B |
| OR003 | DV003 | BG005 | PATIENT_C |
| OR003 | DV003 | BG006 | PATIENT_C |
| OR003 | DV003 | BG007 | PATIENT_C |
| EQ210 | DIAL032 | BG008 | PATIENT_D |

Fig. 9

BEACON-BASED SYSTEMS AND METHODS FOR COMMUNICATIVELY PAIRING A DEVICE WITH A MEDICAL SYSTEM

RELATED APPLICATIONS

The present application is a U.S. National Stage Application under 35 U.S.C. § 371 of International Application No. PCT/US2020/062065, filed on Nov. 24, 2020, which claims priority to U.S. Provisional Patent Application No. 62/940,792, filed on Nov. 26, 2019, and to U.S. Provisional Patent Application No. 62/940,794, filed on Nov. 26, 2019, the contents of which are hereby incorporated by reference in their entireties.

BACKGROUND INFORMATION

In a medical facility (e.g., a hospital, a nursing home, etc.), medical personnel may use a medical system to diagnose, treat, and/or assist patients. In some medical facilities the medical personnel may also use a user device (e.g., a tablet computer, a smartphone, etc.) in the diagnosis, treatment, and/or assistance of the patient. For example, during a computer-assisted surgical procedure, such as a minimally invasive surgical procedure performed at a surgical facility, a surgeon may interact with a computer-assisted surgical system to control teleoperated surgical instruments to perform the surgical procedure on a patient. Other surgical team members may also interact with the computer-assisted surgical system to assist with the surgical procedure. A surgical team member (e.g., a nurse) may use an auxiliary device (e.g., a mobile device) during the surgical procedure, such as to view information about the patient or the computer-assisted surgical system, There is a need to facilitate the use of an auxiliary device in conjunction with use of a medical system and to ensure that the auxiliary device receives and provides accurate and relevant information.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to determine that an auxiliary device detects an ultrasonic beacon emitted by a beacon generator, identify, in response to the determination that the auxiliary device detects the ultrasonic beacon, a medical system associated with the ultrasonic beacon, and communicatively pair, in response to the identification of the medical system, the auxiliary device with the identified medical system.

Another exemplary system may comprise a memory storing instructions and a processor communicatively coupled to the memory and configured to execute the instructions to determine that an auxiliary device detects a first set of ultrasonic beacons included in a plurality of ultrasonic beacons emitted by a plurality of beacon generators, identify, in response to the determination that the auxiliary device detects the first set of ultrasonic beacons, a medical system associated with the first set of ultrasonic beacons included in the plurality of ultrasonic beacons, and communicatively pair, in response to the identification of the medical system associated with the first set of ultrasonic beacons, the auxiliary device with the medical system.

An exemplary method may comprise determining, by a device pairing system, that an auxiliary device detects an ultrasonic beacon emitted by a beacon generator, identifying, by the device pairing system in response to the determination that the auxiliary device detects the ultrasonic beacon, a medical system associated with the ultrasonic beacon, and communicatively pairing, by the device pairing system in response to the identification of the medical system, the auxiliary device with the identified medical system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary medical facility association table according to principles described herein.

DETAILED DESCRIPTION

Figure 1:
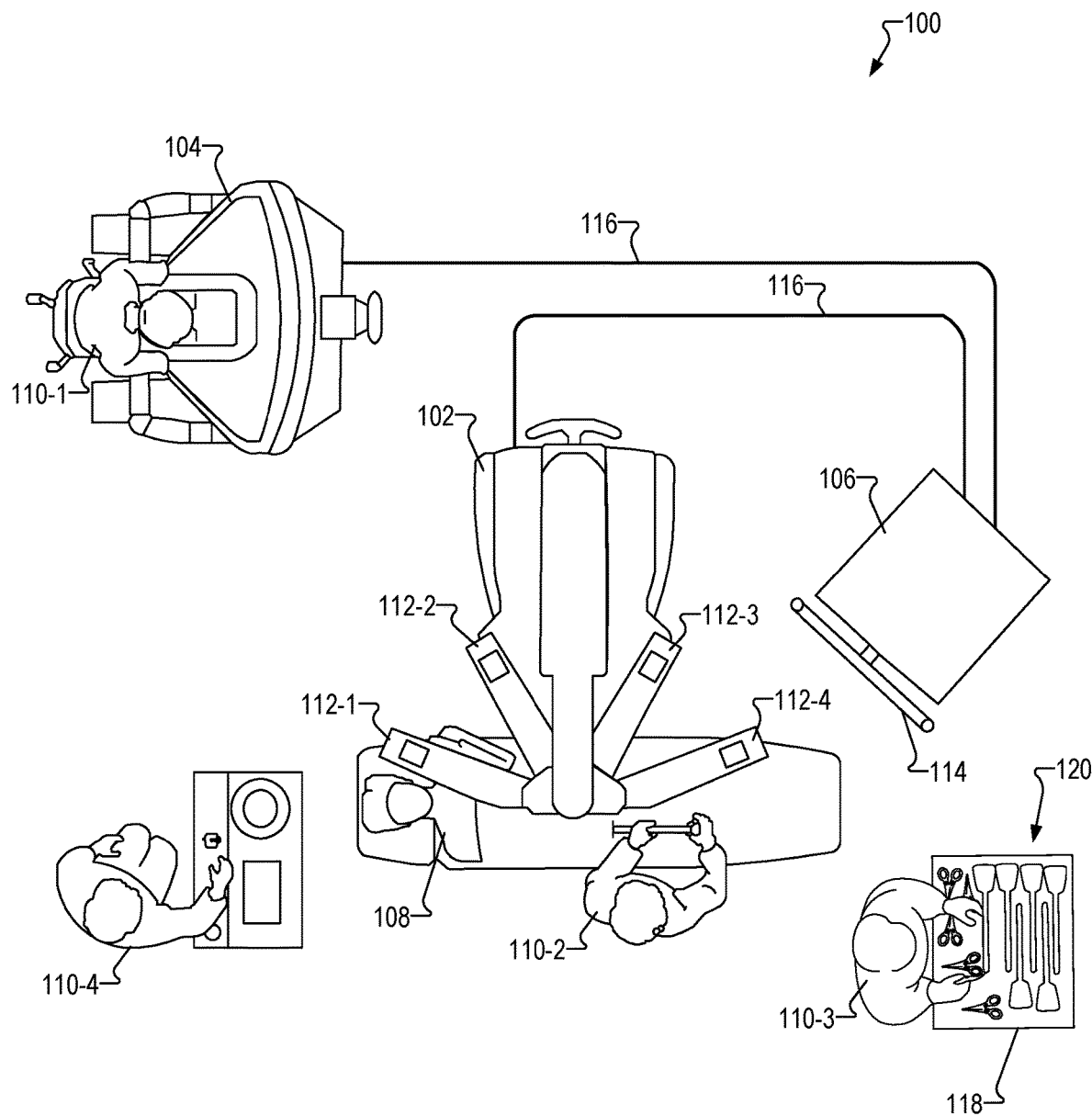
FIG. 1 illustrates an exemplary computer-assisted surgical system according to principles described herein

Device pairing systems and methods are described herein. As will be described below in more detail, a device pairing system may determine that an auxiliary device detects an ultrasonic beacon emitted by a beacon generator. In response to the determination that the auxiliary device detects the ultrasonic beacon, the device pairing system may identify a medical system associated with the ultrasonic beacon. In response to the identification of the medical system, the device pairing system may communicatively pair the auxiliary device with the identified medical system.

To illustrate, an operating room in a hospital may contain a computer-assisted surgical system and a beacon generator. The beacon generator may be a standalone device (e.g., mounted to an operating room wall or ceiling) or may be integrated within the computer-assisted surgical system. The beacon generator may emit a unique ultrasonic beacon that includes identification information that identifies, for example, the computer-assisted surgical system or the operating room in which the computer-assisted surgical system is located.

When a surgical team member (e.g., a nurse) enters the operating room with his/her mobile device (e.g., a tablet computer), the mobile device may detect (by way of a microphone) the ultrasonic beacon emitted by the beacon generator. A mobile device pairing system may determine that the mobile device detects the ultrasonic beacon. In response, the mobile device pairing system may use the identification information included in the ultrasonic beacon to identify the computer-assisted surgical system as being associated with the ultrasonic beacon. The mobile device pairing system may then communicatively pair the mobile device with the computer-assisted surgical system.

Upon pairing, the surgical team member may gain access, by way of the mobile device, to one or more functional features associated with the computer-assisted surgical system. For example, the surgical team member may, by way of the mobile device, exchange data and content (e.g., an endoscopic video stream) with the computer-assisted surgical system, control one or more features or settings of the computer-assisted surgical system, view information about the current surgical procedure performed with the computer-assisted surgical system (e.g., patient information, surgical team information, etc.), and/or communicate with other mobile devices of surgical team members assisting with the surgical procedure.

In some examples a medical system may be associated with multiple unique ultrasonic beacons and the device pairing system may communicatively pair the auxiliary device with the medical system only when the auxiliary device detects the multiple unique ultrasonic beacons associated with the medical system. For example, the pairing may occur only when the auxiliary device detects a unique ultrasonic beacon associated with each component of a computer-assisted surgical system (e.g., a user control system, a manipulating system, and an auxiliary system). In this way the device pairing system can prevent false-positive determinations based on stray ultrasonic beacons, such as when the auxiliary device detects an ultrasonic beacon from an adjoining operating room.

The systems and methods described herein may provide various benefits. For example, the systems and methods described herein may automatically pair an auxiliary device with a medical system when the auxiliary device is in physical proximity to the medical system. This automatic pairing can greatly improve convenience to the user of the auxiliary device and allow the user to focus on a medical procedure. Additionally, the systems and methods described herein pair an auxiliary device with a medical system only when the auxiliary device is in the same physical area (e.g., an operating room) as the medical system, thereby ensuring that the user gains access, by way of the auxiliary device, to functional features associated with the medical system only when the auxiliary device is in physical proximity to the medical system. These and other benefits of the systems and methods described herein will be made apparent in the description that follows.

The pairing systems and methods described herein may be implemented as part of or in conjunction with a medical system, such as a computer-assisted surgical system. As such, an exemplary computer-assisted surgical system will now be described. The following exemplary computer-assisted surgical system is illustrative and not limiting, as the device pairing systems and methods described herein may be implemented as part of or in conjunction with other suitable medical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. In some examples, surgical system 100 may be implemented by one or more of these components. However, surgical system 100 is not limited to these components, and may include additional components as may suit a particular implementation, such as but not limited to a patient operating table, third-party components (e.g., electrosurgical units) connected to surgical system 100, and the like.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, and/or treat a physical condition of the patient. Additionally, a surgical procedure may include any non-clinical procedure, e.g., a procedure that is not performed on a live patient, such as a calibration or testing procedure, a training procedure, and an experimental or research procedure.

As shown in FIG. 1, manipulating system 102 may include a plurality of manipulator arms 112 (e.g., manipulator arm 112-1 through 112-4) to which a plurality of surgical instruments (not shown in FIG. 1) may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 108 and manipulated to perform a computer-assisted surgical procedure on patient 108). In some examples, one or more of the surgical instruments may include force-sensing and/or other sensing capabilities. While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 112, surgical instruments coupled to manipulator arms 112, and/or any other components of manipulating system 102 (e.g., boom arms). One or more components of surgical system 100 may be configured to use the kinematics information to track (e.g., determine poses, movements, and/or states of) and/or control manipulator arms 112 and/or surgical instruments. Manipulating system 102 may also include other sensors configured to generate other information as may suit a particular implementation. Such sensors may also be referred to as "surgical system sensors" and may include, for example, draping sensors, boom height sensors, and the like.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of surgical system 100 (e.g., manipulator arms 112 and surgical instruments attached to manipulator arms 112). For example, surgeon 110-1 may interact with user input devices included in user control system 104 to remotely move or manipulate manipulator arms 112 and the surgical instruments coupled to manipulator arms 112. To this end, user control system 104 may provide surgeon 110-1 with imagery (e.g., high-definition stereoscopic imagery) of a surgical area associated with patient 108 as captured by an imaging device (e.g., a stereoscopic endoscope). Surgeon 110-1 may utilize the imagery to perform one or more procedures with one or more surgical instruments coupled to manipulator arms 112.

To facilitate control of surgical instruments, user control system 104 may include a set of master controls (not shown in FIG. 1). These master controls may be manipulated by surgeon 110-1 to control movement of surgical instruments (e.g., by utilizing robotic and/or teleoperation technology).

The master controls may be configured to detect a wide variety of hand, wrist, and finger movements by surgeon 110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more additional user input devices (e.g., foot pedals, buttons, switches, touchscreen displays, etc.) configured to receive manual input from surgeon 110-1, In some examples, user control system 104 may also include one or more audio input devices (e.g., microphones) configured to receive audio input (e.g., voice input) from one or more users, and one or more audio output devices (e.g., speakers).

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102 (e.g., from an imaging device), and process image data representative of imagery captured by an endoscope attached to a manipulator arm 112.

In some examples, auxiliary system 106 may be configured to present visual content to surgical team members 110 who may not have access to the imagery provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

While auxiliary system 106 is shown in FIG. 1 as a separate system from manipulating system 102 and user control system 104, auxiliary system 106 may be included in, or may be distributed across, manipulating system 102 and/or user control system 104. Additionally, while user control system 104 has been described as including one or more user input devices and/or audio input devices, other components of surgical system 100 (e.g., manipulating system 102 and/or auxiliary system 106) may include user input devices, audio input devices, and/or audio output devices as may suit a particular implementation.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any optical, wired, or wireless communication link as may serve a particular implementation. To this end, manipulating system 102, user control system 104, and auxiliary system 106 may each include one or more optical, wired, or wireless communication interfaces, such as one or more local area network interfaces, Wi-Fi network interfaces, cellular interfaces, etc.

As shown in FIG. 1 system 100 may also include an accessory cart 118. Accessory cart 118 may be configured to carry or store certain accessories of surgical system 100 and/or supplies to be used during the surgical procedure. For example, accessory cart 118 may hold surgical instruments 120 that may be coupled with manipulator arms 112 as needed during the surgical procedure.

In alternative embodiments, accessory cart 118 is not included in system 100 but is a standalone medical system. For example, accessory cart 118 may be used to deliver sterilized instruments from a sterile processing department ("SPD") of a hospital to various operating rooms throughout the hospital. Thus, in these embodiments accessory cart 118 is not included in system 100 but may be a separate medical system.

In some examples a medical system (e.g., surgical system 100, accessory cart 118, etc.) may be located within a medical facility that uses one or more ultrasonic beacons to facilitate communicative pairing of one or more devices with the medical system and/or to provide contextual information about the medical system, such as information about a medical procedure performed with the medical system, the location of the medical system, errors of the medical system, and the like.

Figure 2:
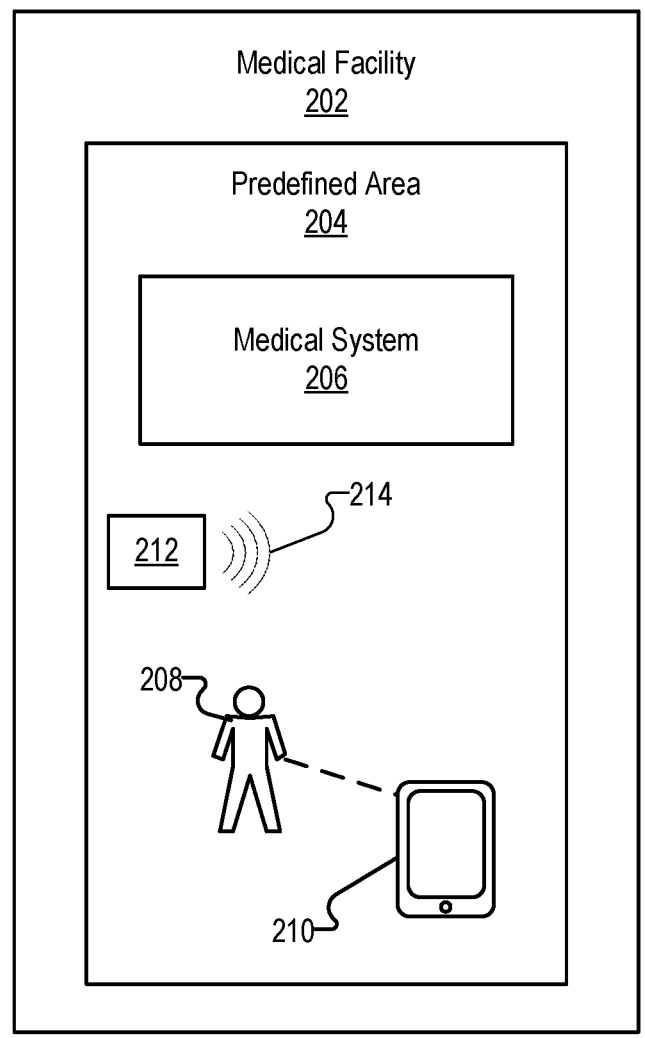
FIGS. 2-6 illustrate exemplary configurations of a medical facility including one or more beacon generators located within a predefined area according to principles described herein.

FIG. 2 illustrates an exemplary configuration 200 of a medical facility 202. As shown, medical facility 202 includes a predefined area 204 and a medical system 206 located within predefined area 204. Medical facility 202 may be, for example, a hospital, a unit within a hospital (e.g., an emergency room, a trauma center, a maternity unit, an intensive care unit, etc.), a surgical facility, a deployable field hospital, a medical clinic, a doctor's office, a dentist's office, a nursing home, a hospice facility, a rehab facility, an assisted living facility, or any other similar facility, Predefined area 204 is a particular area (e.g., a particular room) within medical facility 202 in which medical system 206 is located and/or used to perform one or more tasks or operations with respect to a patient. For example, predefined area 204 may be an operating room, a recovery room, a consulting room, a patient room, an examination room, an equipment room, and the like. In some examples predefined area 204 is defined by and/or separated from other areas of medical facility 202 (e.g., from an adjoining operating room, from a hallway, from an equipment room, etc.) by one or more physical barriers (e.g., walls, windows, doors, curtains, etc.).

Medical system 206 may be any type of medical system that may be used to monitor, treat, and/or assist a patient located within medical facility 202. For example, medical system 206 may be a surgical system (e.g., a computer-assisted surgical system, such as surgical system 100), an imaging system (e.g., a computed tomography (CT) scanner, a magnetic resonance imaging (MRI) scanner, an X-ray machine, etc.), a dialysis machine, a heart-lung machine, a monitoring device (e.g., a heartrate monitor, a blood pressure monitor, etc.), a ventilator, a patient bed, an accessory cart, and the like. In some examples medical system 206 is a mobile accessory cart (e.g., accessory cart 118) that may move throughout medical facility 202. For example, a mobile accessory cart may be an SPD cart that may be used to deliver sterilized instruments throughout medical facility 202 (e.g., to distribute sterilized instruments to various operating rooms).

Medical system 206 may be configured to communicatively pair with an auxiliary device when the auxiliary device is in proximity to medical system 206. An auxiliary device may be any device that may communicate, directly or indirectly, with medical system 206, such as a user device, a medical device, a component of a medical system (e.g., manipulating system 102, user control system 104, auxiliary system 106, etc.), an accessory cart, and any other suitable device.

For example, as shown in FIG. 2, a user 208 (e.g., a surgical team member 110) located within medical facility 202 may gain access, by way of a user device 210, to one or more functional features (e.g., an endoscopic video feed, a settings menu, medical system controls, etc.) associated with medical system 206 when user device 210 is communicatively paired with medical system 206. For instance, the user may, by way of an application executed by user device 210, view content associated with medical system 206, interact with medical system 206, and/or communicate with other users via additional user devices that are communicatively paired with medical system 206. In the exemplary embodiments described herein and shown in the figures the auxiliary device is implemented by user device 210. However, it will be appreciated that the auxiliary device may be implemented additionally or alternatively by any other auxiliary device as may suit a particular implementation. Even when user device 210 is not communicatively paired with medical system 206, user 208 may have access to other functional features associated with medical facility 202. For example, the user may, by way of an application executed by user device 210, view and/or edit medical personnel information, update user profile information, view training content, schedule tasks, schedule medical procedures, view patient information, and the like. While FIG. 2 shows that the auxiliary device is implemented by user device 210, in other implementations the auxiliary may be any other suitable auxiliary device.

User device 210 may be any device capable of presenting information to a user, whether in visual, audio, or haptic format, and/or receiving user input from user 208. For example, user device 210 may be implemented by a mobile device (e.g., a mobile phone, a handheld device, a tablet computing device, a laptop computer, a personal computer, etc.), an audio device (e.g., a speaker, earphones, etc.), a wearable device (e.g., a smartwatch device, an activity tracker, a head-mounted display device, a virtual or augmented reality device, etc.), and/or a display device (e.g., a television, a projector, a monitor, a touch screen display device, etc.).

To facilitate communicative pairing of user device 210 with medical system 206 and/or to convey contextual information about medical system 206, a beacon generator 212 (e.g., an ultrasonic transducer) is located within predefined area 204 and configured to generate and emit an ultrasonic beacon 214 that is associated with medical system 206. Ultrasonic beacon 214 comprises sound waves generally having a frequency above the human audible hearing range (e.g., above about 17 kHz). In some examples, ultrasonic beacon 214 has a frequency between about 17 kHz and about 20 kHz.

Ultrasonic beacon 214 may include repeated transmissions of a particular message. For each transmission of ultrasonic beacon 214, beacon generator 212 may include (e.g., encode) the message in ultrasonic beacon 214 by modulating one or more of the amplitude, frequency, and waveform of ultrasonic signals, such as by using phase-shift keying (PSK), binary phase-shift keying (BPSK), quadrature phase-shift keying (QPSK), amplitude-shift keying (ASK), frequency shift keying (FSK), on-off keying (OOK), quadrature amplitude modulation (QAM), an audio QR code format, by multi-frequency bit-coding, or any other suitable modulation technique.

In some examples, such as when the information included in ultrasonic beacon 214 has a small bit size, ultrasonic beacon 214 is transmitted over a single channel (e.g., in a single carrier communication scheme). In other examples, such as when the information included in ultrasonic beacon 214 has a large bit-size (e.g., 32 bits, 64 bits, etc.), ultrasonic beacon 214 is transmitted over multiple subchannels in a multi-carrier communication scheme (e.g., frequency division multiplexing (FSM), orthogonal frequency division multiplexing modulation (OFDM)), In a multi-carrier communication scheme, each transmission of ultrasonic beacon 214 includes an information signal in which the message is encoded and a pilot signal for synchronization of transmissions of ultrasonic beacon 214. As will be explained below in more detail, subchannel cycling may be used in a multi-carrier communication scheme to allow the information in ultrasonic beacon 214 to be recovered even when the signal quality in some of the subchannels is poor or corrupt or the signal is lost.

The message included (e.g., encoded) in ultrasonic beacon 214 may include information (e.g., contextual information and/or identification information) associated with medical system 206. In some examples, the information encoded in ultrasonic beacon 214 associates, or may be used to associate, ultrasonic beacon 214 with medical system 206. For example, ultrasonic beacon 214 may include a location identifier that identifies the predefined area (i.e., predefined area 204) in which ultrasonic beacon 214 is located. The location identifier may be, for example, a unique identification ("ID") number (e.g., a room number) assigned to or otherwise representative of predefined area 204. As another example, ultrasonic beacon 214 may include a medical system identifier (e.g., a surgical system identifier) that identifies the medical system (i.e., medical system 206) with which ultrasonic beacon 214 is associated. The medical system identifier may be, for example, a unique medical system ID assigned to or otherwise representative of medical system 206. Additionally or alternatively, the medical system identifier may be a network address for the medical system. As yet another example, ultrasonic beacon 214 may include a beacon generator identifier that identifies the particular beacon generator (i.e., beacon generator 212) that emits ultrasonic beacon 214. The beacon generator identifier may be a beacon generator ID assigned to or otherwise representative of beacon generator 212. As a further example, ultrasonic beacon 214 may include a medical session identifier that identifies a particular medical session with which ultrasonic beacon 214 is associated. The medical session identifier may be a medical session ID assigned to or otherwise representative of a particular medical session (e.g., a patient ID, medical team personnel IDs, a surgeon ID, a room ID, a surgical session ID, etc.). In some examples, the identification information may comprise a combination of letters and numbers (e.g., a 10-digit number). It will be recognized that the foregoing information that may be included in ultrasonic beacon 214 is merely illustrative and not limiting, as ultrasonic beacon 214 may include any other suitable information (e.g., GPS coordinates, error information, status information, etc.).

In some examples, the message encoded in ultrasonic beacon 214 may also include validation information (e.g., a parity bit, an error detection code, an error-correcting code, etc.). As will be explained below in more detail, the validation information may be used for validation of ultrasonic beacon 214 when ultrasonic beacon 214 is detected by another device.

User device 210 is configured to detect (e.g., via a microphone, an ultrasonic sensor, etc.) ultrasonic beacon 214 when user device 210 is in proximity to beacon generator 212. In some examples, ultrasonic beacon 214 is configured to not transmit through solid barriers (e.g., walls) and/or is configured to be confined within predefined area 204. Accordingly, user device 210 may detect ultrasonic beacon 214 only when user device 210 is located within the same predefined area 204 (e.g., operating room) as beacon generator 212, as shown in FIG. 2. When user device 210 is not located within predefined area 204, user device 210 does not detect ultrasonic beacon 214. Examples of user device 210 detecting ultrasonic beacon 214 will be described below in more detail.

As shown in FIG. 2, beacon generator 212 is a standalone device separate from medical system 206 (e.g., beacon generator 212 is not physically integrated with or controlled by medical system 206). As a standalone device beacon generator 212 may be fixedly positioned at any suitable location within predefined area 204, such as on a wall or ceiling of predefined area 204. Alternatively, beacon generator 212 may be a movable standalone device that may be moved and positioned as desired within predefined area 204 and/or within medical facility 202.

Figure 3:
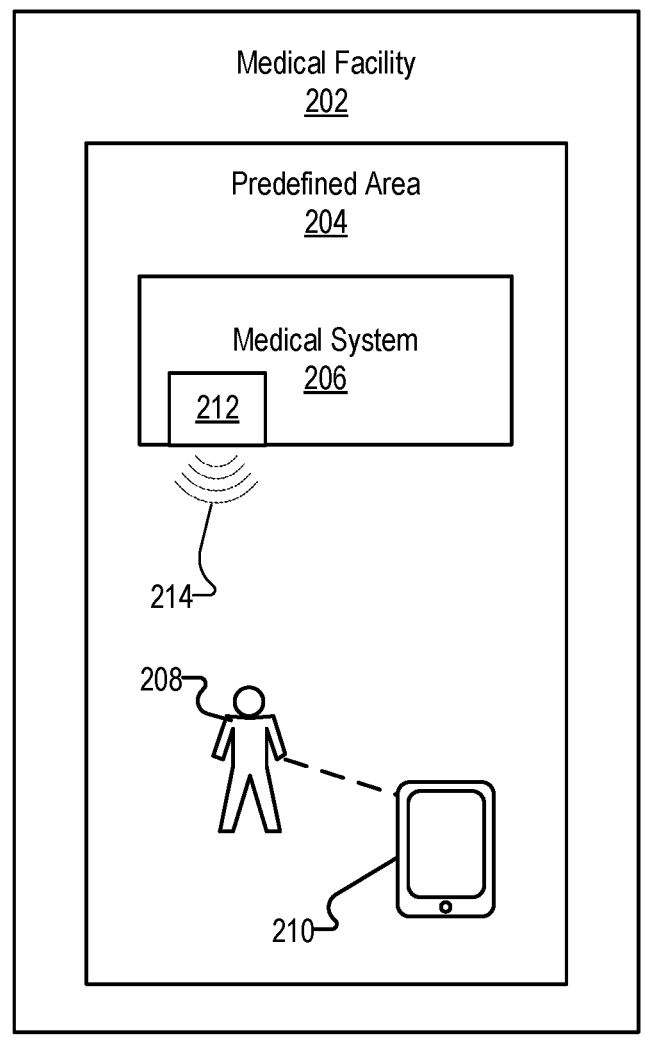

Alternatively to a standalone device separate from medical system 206, beacon generator 212 may be included in medical system 206, as shown in FIG. 3. FIG. 3 illustrates another exemplary configuration 300 of medical facility 202. FIG. 3 is similar to FIG. 2 except that in FIG. 3 beacon generator 212 is included in medical system 206. Beacon generator 212 may be included in medical system 206 in any suitable way. For example, beacon generator 212 may be physically integrated with medical system 206 (e.g., mounted on a column of manipulating system 102, included in user control system 104, etc.). Thus, if medical system 206 is moved to a different area of medical facility 202, beacon generator 212 also moves to the new area. Additionally or alternatively, beacon generator 212 may be controlled by medical system 206. For example, medical system 206 (e.g., auxiliary system 106 of surgical system 100) may configure ultrasonic beacon 214 to include information and may control the emission of ultrasonic beacon 214 by beacon generator 212.

Figure 4:
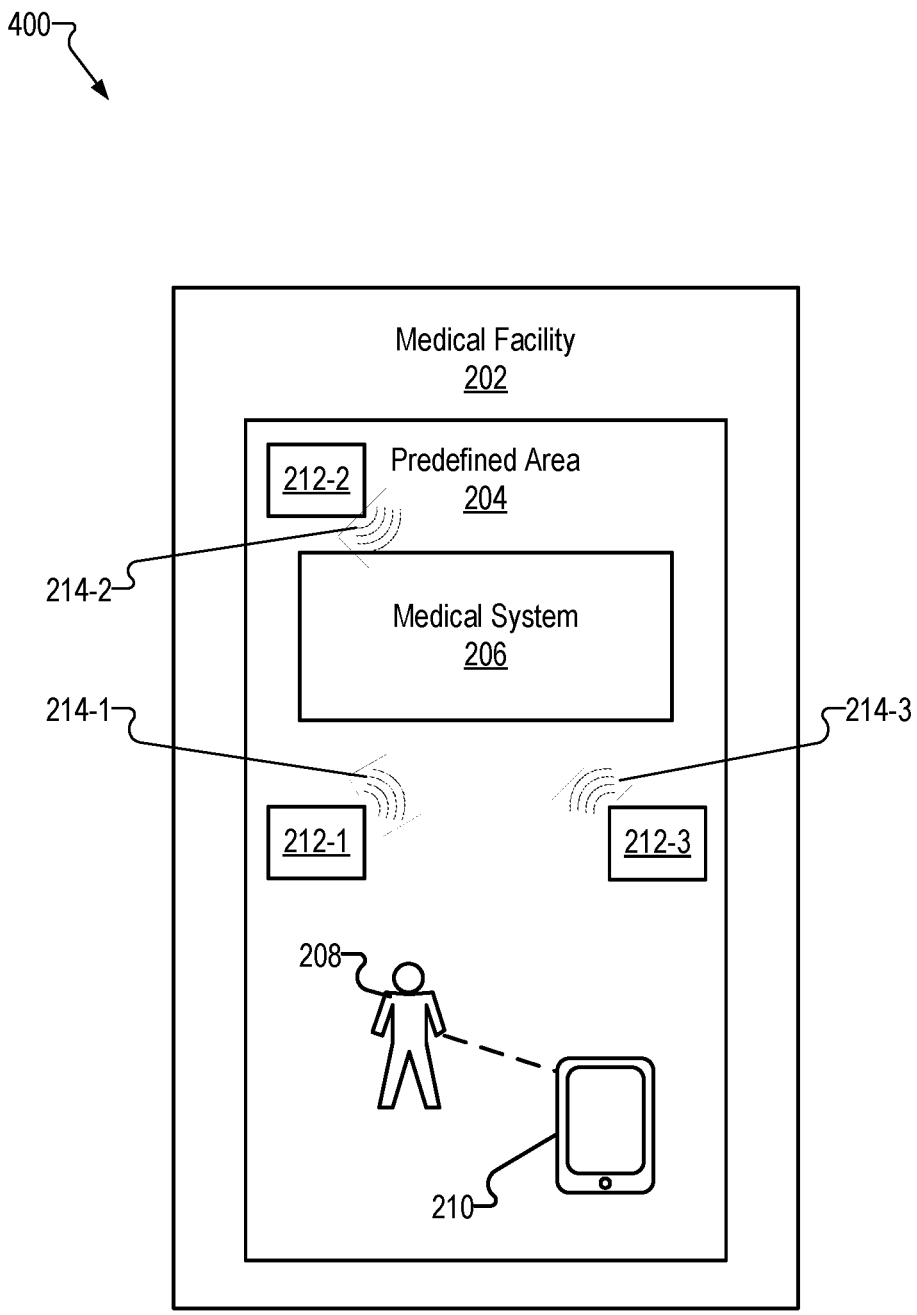

The exemplary configurations 200 and 300 of medical facility 202 described above include a single beacon generator 212 located within predefined area 204. However, multiple beacon generators 212 may be located within predefined area 204, as illustrated in FIG. 4. FIG. 4 illustrates another exemplary configuration 400 of medical facility 202. FIG. 4 is similar to FIG. 2 except that in FIG. 4 predefined area 204 includes three beacon generators 212 (e.g., beacon generators 212-1 through 212-3) configured to emit ultrasonic beacons 214 (e.g., ultrasonic beacons 214-1 through 214-3) associated with medical system 206. It will be recognized, however, that predefined area 204 may include any other number of beacon generators 212 as may suit a particular implementation.

Ultrasonic beacons 214 may each include information (e.g., information encoded in an information signal of ultrasonic beacon 214) that may be used by a device pairing system to identify a particular medical system (i.e., medical system 206) that is associated with ultrasonic beacons 214, to control communicative pairing of user device 210 with medical system 206, and/or to control the performance of operations associated with medical system 206. In some examples ultrasonic beacons 214 each include the same information (e.g., the same location ID). In additional or alternative examples, each ultrasonic beacon 214 includes unique identification information. For example, ultrasonic beacon 214-1 may include a surgical system identifier, ultrasonic beacon 214-2 may include a location identifier, and ultrasonic beacon 214-3 may include a patient identifier. In some examples one or more beacon generators 212 (or components or devices connected to or associated with beacon generators 212) may be configured to listen for and detect ultrasonic beacons 214 emitted by the other beacon generators 212 located within predefined area 204 and use the detected ultrasonic beacons 214 to coordinate transmission of ultrasonic beacons 214 so as to avoid or minimize interference.

Figure 5:
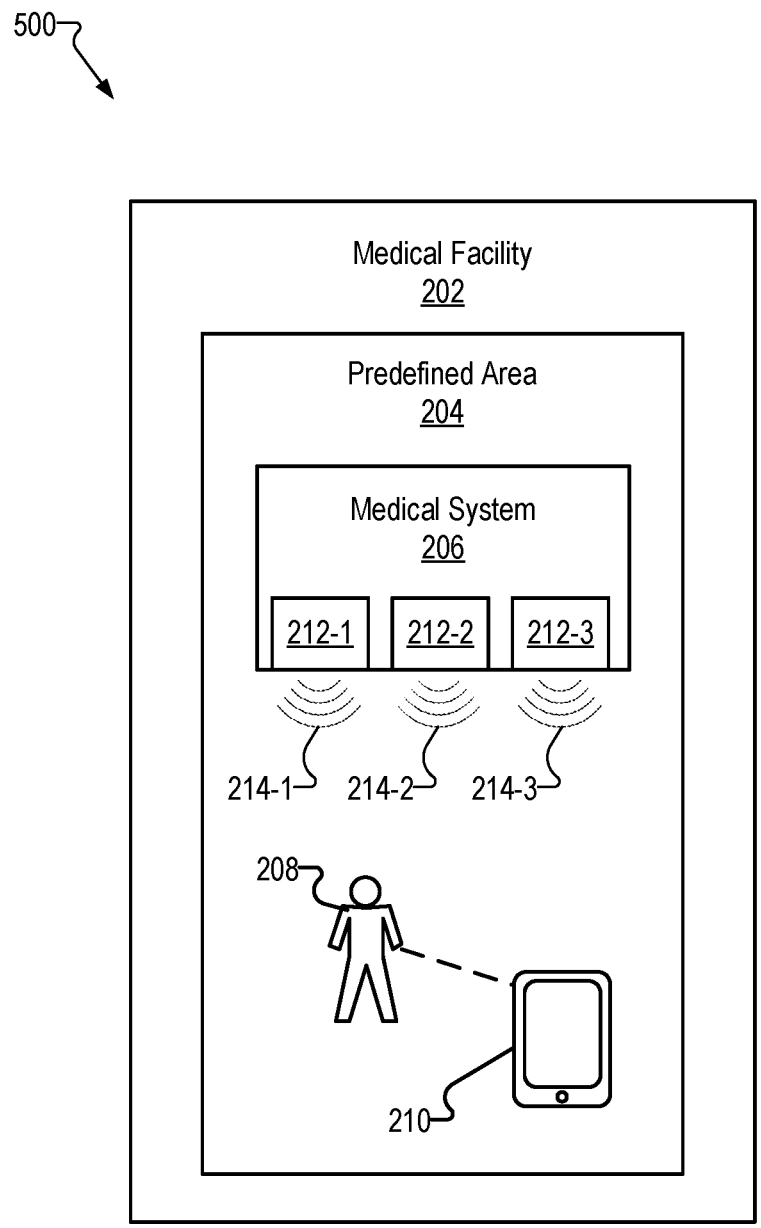

In some examples multiple beacon generators 212 may be included in medical system 206, as shown in FIG. 5. FIG. 5 illustrates another exemplary configuration 500 of medical facility 202. FIG. 5 is similar to FIG. 4 except that beacon generators 212 (e.g., beacon generators 212-1 through 212-3) are included in medical system 206. Beacon generators 212 may be included in medical system 206 in any suitable way. For example, beacon generators 212 may be physically integrated with and/or controlled by medical system 206, as explained above. In some examples each beacon generator 212 is included in a different component of medical system 206. For instance, if medical system 206 is implemented by surgical system 100, beacon generator 212-1 may be included in manipulating system 102, beacon generator 212-2 may be included in user control system 104, and beacon generator 212-3 may be included in auxiliary system 106.

In some examples ultrasonic beacons 214 include the same information (e.g., the same medical system ID). In additional or alternative examples, each ultrasonic beacon 214 includes unique information. For example, when medical system 206 includes multiple components, various components may each include a beacon generator 212 and each ultrasonic beacon 214 may include a unique component identifier (e.g., a component ID) assigned to or otherwise representative of the particular component in which the beacon generator 212 is included. For instance, referring again to the example in which medical system 206 is implemented by surgical system 100, ultrasonic beacon 214-1 may include a unique component ID for manipulating system 102, ultrasonic beacon 214-2 may include a unique component ID for user control system 104, and ultrasonic beacon 214-3 may include a unique component ID for auxiliary system 106.

Figure 6:
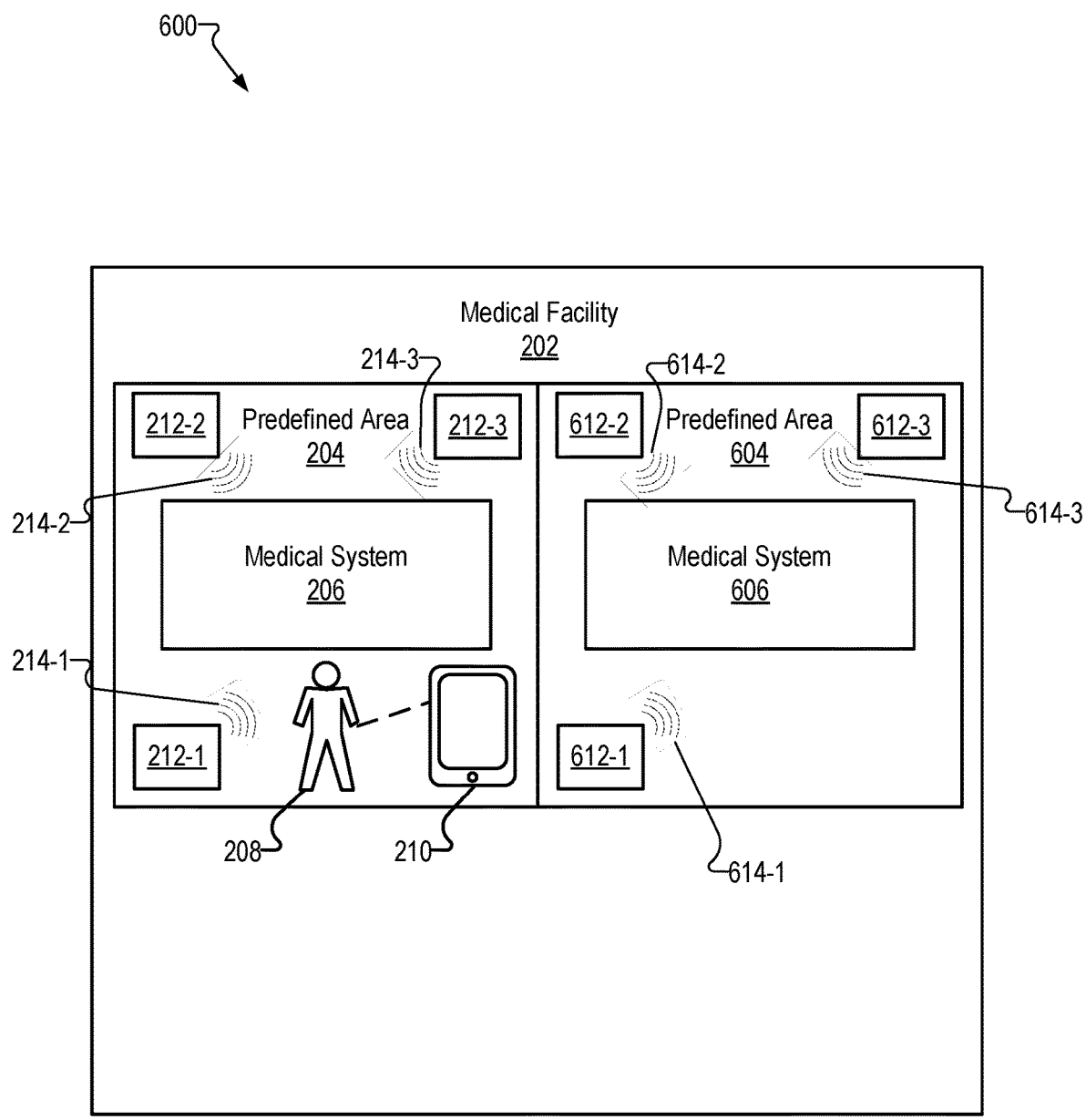

In some configurations, medical facility 202 may also include additional beacon generators (not shown in FIGS. 4 and 5) in areas outside of predefined area 204, as illustrated in FIG. 6. FIG. 6 illustrates another exemplary configuration 600 of medical facility 202. FIG. 6 is similar to FIG. 4 except that in FIG. 6 medical facility 202 includes an additional predefined area 604 adjoining predefined area 204, an additional medical system 606 located in predefined 604, and additional beacon generators 612 (e.g., beacon generators 612-1 through 612-3) located within predefined area 604 and that emit ultrasonic beacons 614 (e.g., ultrasonic beacons 614-1 through 614-3) associated with additional medical system 606. It will be recognized that any of beacon generators 212-1 through 212-3 may alternatively be included in medical system 206, and any of beacon generators 612-1 through 612-3 may alternatively be included in medical system 612, in the manner described above with reference to FIG. 5. Additionally, predefined areas 204 and 604 may each include any other number of beacon generators 212 and 612, respectively, as may suit a particular implementation.

It will be recognized that the foregoing configurations of medical facility 202 are merely illustrative and not limiting, as medical facility 202 may include any number and configuration of predefined areas, medical systems, and beacon generators as may suit a particular implementation. Moreover, any of the configurations described herein may be modified or combined as may suit a particular implementation.

Figure 7:
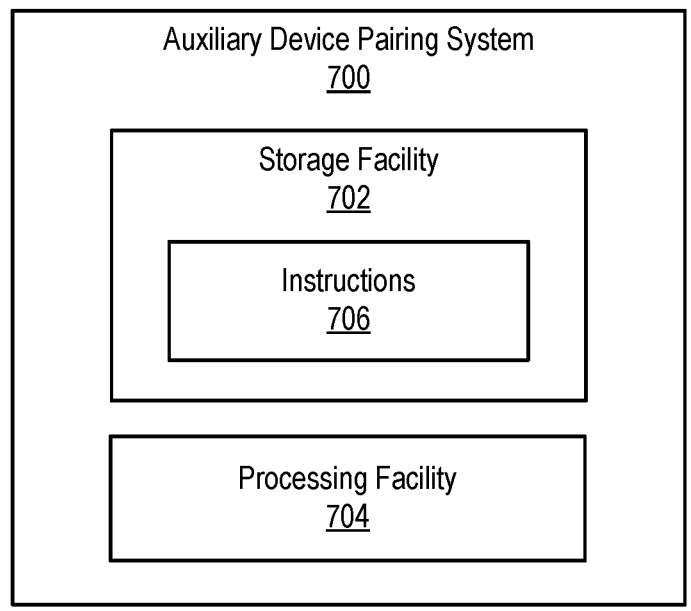
FIG. 7 illustrates an exemplary device pairing system according to principles described herein.

As mentioned, ultrasonic beacons 214 may include information that may be used by a device pairing system to facilitate and/or control communicative pairing of an auxiliary device (e.g., user device 210) with a medical system (e.g., medical system 206) that is associated with ultrasonic beacons 214. Ultrasonic beacons 214 may additionally or alternatively include information that may be used by a device pairing system to control performance of an operation associated with medical system 206. FIG. 7 illustrates an exemplary device pairing system 700 ("pairing system 700") that may be configured to communicatively pair a device with a medical system and/or to control performance of an operation associated with a medical system. Pairing system 700 may be included in, implemented by, or connected to any medical systems or other computing systems described herein. For example, pairing system 700 may be implemented by a computer-assisted surgical system (e.g., surgical system 100). As another example, pairing system 700 may be implemented by a stand-alone computing system communicatively coupled to a medical system. In some examples pairing system 700 may be implemented, in whole or in part, by a device (e.g., user device 210).

As shown in FIG. 7, pairing system 700 includes, without limitation, a storage facility 702 and a processing facility 704 selectively and communicatively coupled to one another. Facilities 702 and 704 may each include or be implemented by hardware and/or software components (e.g., processors, memories, communication interfaces, instructions stored in memory for execution by the processors, etc.). For example, facilities 702 and 704 may be implemented by any component in a medical system. In some examples, facilities 702 and 704 may be distributed between multiple devices and/or multiple locations as may serve a particular implementation.

Storage facility 702 may maintain (e.g., store) executable data used by processing facility 704 to perform any of the operations described herein. For example, storage facility 702 may store instructions 706 that may be executed by processing facility 704 to perform any of the operations described herein. Instructions 706 may be implemented by any suitable application, software, code, and/or other executable data instance. Storage facility 702 may also maintain any data received, generated, managed, used, and/or or transmitted by processing facility 704.

Processing facility 704 may be configured to perform (e.g., execute instructions 706 stored in storage facility 702 to perform) various operations associated with pairing an auxiliary device with a medical system. For example, processing facility 704 may be configured to determine that an auxiliary device detects an ultrasonic beacon emitted by a beacon generator. Processing facility 704 may identify, in response to the determination that the auxiliary device detects the ultrasonic beacon, a medical system associated with the ultrasonic beacon. In response to the identification of the medical system associated with the ultrasonic beacon, processing facility 704 may communicatively pair the auxiliary device with the identified medical system. These and other operations that may be performed by processing facility 704 are described herein. In the description that follows, any references to operations performed by pairing system 700 may be understood to be performed by processing facility 704 of pairing system 700.

In some examples, pairing system 700 is implemented entirely by the medical system itself. For example, pairing system 700 may be implemented by one or more computing devices included in medical system 206 (e.g., in one or more computing devices included within manipulating system 102, user control system 104, and/or auxiliary system 106 of surgical system 100).

Figure 8:
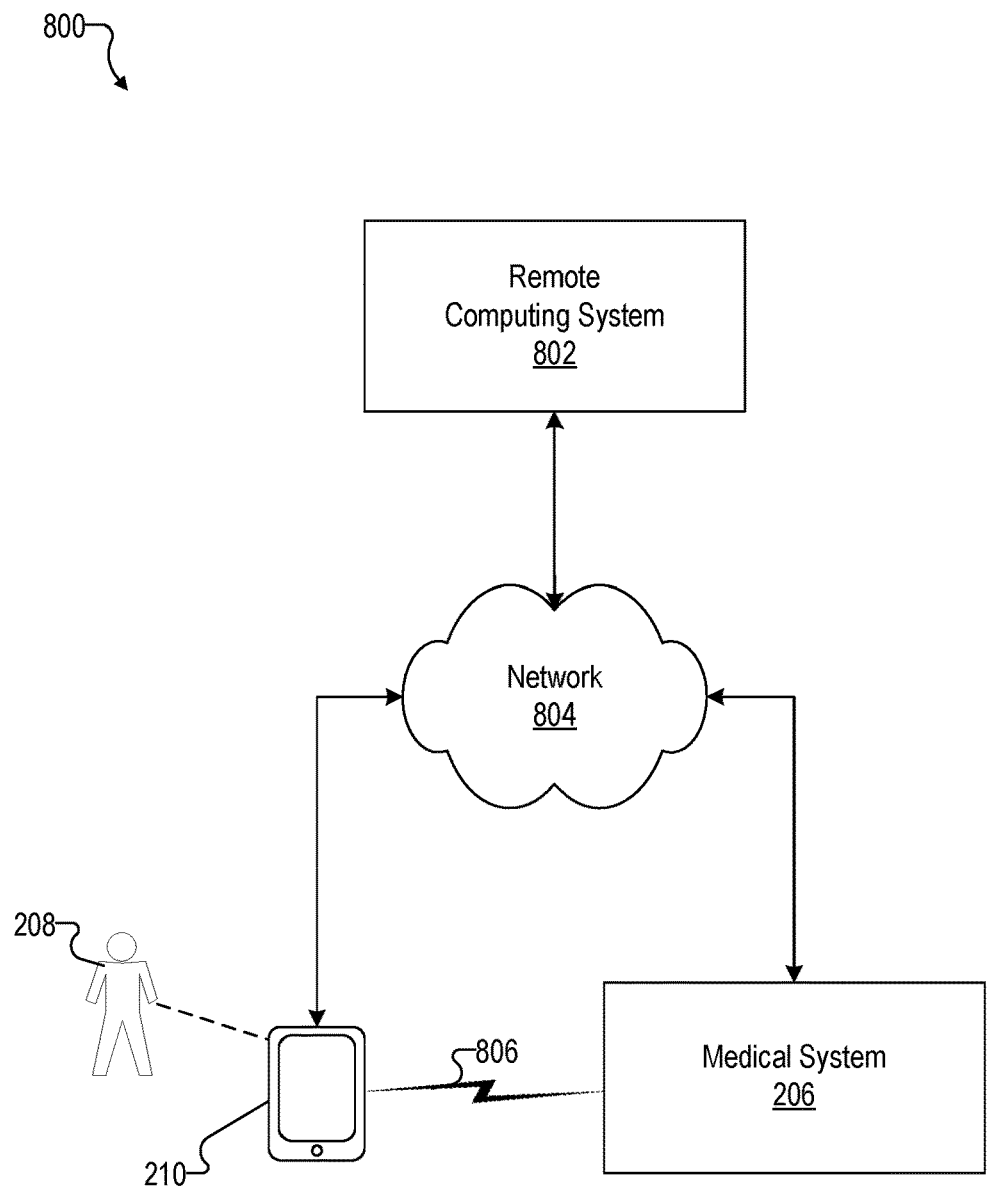
FIG. 8 illustrates an exemplary implementation of the device pairing system of FIG. 7 according to principles described herein.

FIG. 8 illustrates an exemplary implementation 800 of pairing system 700. In implementation 800, a remote computing system 802 may be communicatively coupled to medical system 206 by way of a network 804. Remote computing system 802 may include one or more computing devices (e.g., servers) configured to perform any of the operations described herein.

Network 804 may be a local area network; a wireless network (e.g., Wi-Fi), a wide area network, the Internet, a cellular data network, and/or any other suitable network. Data may flow between components connected to network 804 using any communication technologies, devices; media, and protocols as may serve a particular implementation.

As shown, user device 210 may be connected to network 804 and thereby communicate with remote computing system 802. In some examples, user device 210 may also be communicatively paired with medical system 206. When user device 210 is communicatively paired with medical system 206, user device 210 may be configured to exchange data with medical system 206, thereby enabling user 208 to access, by way of user device 210, one or more functional features associated with medical system 206. User device 210 may be communicatively paired with medical system 206 in any suitable way. For example, user device 210 may be communicatively paired with medical system 206 by way of an indirect communication link (e.g., by way of remote computing system 802 and/or network 804). Alternatively, user device 210 may be communicatively paired with medical system 206 by way of a direct (e.g., peer-to-peer, single hop, or ad hoc) communication link 806. The direct communication link may include, for example, a direct wireless connection, such as a Bluetooth connection, a near field communication connection, a Wi-Fi connection, a Wi-Fi Direct connection, a smartphone ad hoc network (SPAN) connection, a mobile device ad hoc network (MANET) connection, etc. In some examples user device 210 may be communicatively paired with medical system 206 only when user device 210 is physically proximate to medical system 206, such as when user device 210 detects an ultrasonic beacon associated with medical system 206 (e.g., ultrasonic beacon 214). It will be recognized, however, that in some examples user device 210 is not communicatively paired with medical system 206. Communicative pairing of user device 210 with medical system 206 will be described below in more detail.

In some examples remote computing system 802 and/or network 804 are located partly or entirely within a medical facility (e.g., medical facility 202) as part of a medical facility management system (not shown). A medical facility management system may include one or more computing systems configured to generate and/or maintain medical facility data associated with the medical facility and its operations, such as data representative of medical systems included in the medical facility and locations of the medical systems, patient information, beacon generator information and locations of the beacon generators, medical session information, medical personnel information, schedule information, and the like.

In some examples, pairing system 700 is entirely implemented by remote computing system 802 or user device 210. In alternative examples pairing system 700 is distributed across any two or more of remote computing system 802, medical system 206, and user device 210.

Various operations that may be performed by pairing system 700 (e.g., by processing facility 704 of pairing system 700), and examples of these operations, will now be described. It will be recognized that the operations and examples described herein are merely illustrative of the many different types of operations that may be performed by pairing system 700.

As mentioned above, pairing system 700 may determine that an auxiliary device detects an ultrasonic beacon emitted by a beacon generator. The auxiliary device may detect the ultrasonic beacon in any suitable way. For example, the auxiliary device may include a microphone configured to detect ambient sound waves, including the ultrasonic beacon, and process the detected ambient sound waves to generate audio signals representative of the detected ambient sound waves. In some examples an application executed by the auxiliary device may process the audio signals to filter out audio signals that do not meet a predefined set of criteria (e.g., audio signals that are not in the ultrasonic range, do not fall within a predefined amplitude range, etc.). The microphone may also be set, either automatically by the application or manually by a user, to an "always-on" state. In this way the auxiliary device may continually scan for ultrasonic beacons while the auxiliary device is moving throughout a medical facility.

In some examples the auxiliary device (e.g., user device 210) analyzes the audio signals to determine whether the audio signals include an ultrasonic beacon (e.g., whether the audio signals include a pilot signal and/or a message signal). The auxiliary device may use any suitable sound processing algorithm to determine whether the audio signals include an ultrasonic beacon. In response to a determination that the audio signals include an ultrasonic beacon, the auxiliary device may transmit a notification and/or data representative of the ultrasonic beacon to pairing system 700. In response to receipt of the notification and/or the data representative of the ultrasonic beacon, pairing system 700 determines that the auxiliary device detects an ultrasonic beacon.

In alternative examples, pairing system 700 may access the audio signals from the auxiliary device and analyze the accessed audio signals to determine whether the audio signals include an ultrasonic beacon. Pairing system 700 may use any suitable sound processing algorithm to determine whether the audio signals include an ultrasonic beacon. In some examples the auxiliary device may be configured to periodically (e.g., every 5 seconds) transmit the audio signals to pairing system 700. If pairing system 700 determines that the audio signals include an ultrasonic beacon, pairing system 700 determines that the auxiliary device detects an ultrasonic beacon.

Pairing system 700 is further configured to identify, in response to a determination that the auxiliary device detects the ultrasonic beacon, a medical system associated with the ultrasonic beacon. Pairing system 700 may identify a medical system associated with the ultrasonic beacon in any suitable way. In some examples, pairing system 700 may identify a medical system associated with the ultrasonic beacon by decoding the ultrasonic beacon (e.g., the message signal of the ultrasonic beacon) and comparing the information included in the ultrasonic beacon with medical facility data. The medical facility data may take the form of one or more tables or other data structures that associate various attributes of a medical facility, such as predefined areas within the medical facility, medical systems located within the predefined areas of the medical facility, beacon generators located within the predefined areas of the medical facility, and medical sessions being performed within the medical facility and/or with the medical systems. In some examples pairing system 700 may be configured to access the medical facility data from a medical facility management system. Alternatively, the medical facility data may be tracked, generated, and/or maintained by pairing system 700 and/or the auxiliary device.

FIG. 9 illustrates an exemplary medical facility association table 900 ("association table 900") that may be maintained and/or accessed by pairing system 700 in order to identify a medical system associated with a detected ultrasonic beacon. Association table 900 may be configured to specify, for example, which predefined area, medical system, beacon generator, and/or medical session are associated with one another at any given time.

Association table 900 may be configured to specify one or more predefined areas located within a medical facility. For example, as shown in column 902, association table 900 may specify a plurality of location IDs each uniquely identifying a predefined area located within the medical facility.

Association table 900 may be further configured to specify one or more medical systems located within each predefined area. For example, as shown in column 904, a medical system that has a medical system ID of "DV001" is associated with a predefined area that has a location ID of "OR001".

Association table 900 may be further configured to specify one or more beacon generators physically located within each predefined area and/or associated with (e.g., included in) each medical system. For example, as shown in column 906, a beacon generator that has a beacon generator ID of "BG001" is associated with the predefined area that has the location ID of "OR001" and the medical system ID that has the medical system ID of "DV001."

Association table 900 may be further configured to specify a medical session being performed within each predefined area and/or with each medical system. For example, as shown in column 908, a surgical session that has a surgical session ID of "Patient A" is associated with the predefined area that has the location ID of "OR001" and the medical system that has the medical system ID of "DV001."

It will be recognized that association table 900 is not limited to the examples of data shown in FIG. 9, but may include any additional or alternative data as may suit a particular implementation. For example, association table 900 may associate a medical system component ID representative of a particular medical system component (e.g., manipulating system 102, user control system 104, auxiliary system 106, etc.) with a particular location ID, a particular medical system ID, and/or a particular beacon generator ID. Additionally, association table 900 may be dynamically updated as beacon generators or medical systems change locations within the medical facility and as medical sessions change (e.g., start or end).

As mentioned, pairing system 700 may identify a medical system associated with the ultrasonic beacon by comparing information included in the ultrasonic beacon with medical facility data. For example, pairing system 700 may identify a medical system that is physically located within the same predefined area as the beacon generator that emitted the ultrasonic beacon. For instance, pairing system 700 may identify, based on medical facility data, a medical system ID that is directly or indirectly associated with a location ID included in the ultrasonic beacon.

As another example, pairing system 700 may identify a medical system that is being used to perform a medical session that is represented by a medical session identifier included in the ultrasonic beacon. For instance, pairing system 700 may identify, based on medical facility data, a medical system ID that is directly or indirectly associated with a surgical session ID included in the ultrasonic beacon.

As yet another example, pairing system 700 may identify a medical system associated with the beacon generator that emitted the ultrasonic beacon. For instance, pairing system 700 may identify, based on medical facility data, a medical system ID that is directly or indirectly associated with a beacon generator ID included in the ultrasonic beacon.

In some examples pairing system 700 may identify a medical system associated with the ultrasonic beacon by identifying a medical system ID included in the ultrasonic beacon. For example, the beacon generator may be configured to include the medical system ID in the ultrasonic beacon when the medical system and the beacon generator are permanently located within a predefined area, or when the beacon generator is included in the medical system.

In response to identification of a medical system associated with the ultrasonic beacon, pairing system 700 may communicatively pair the auxiliary device with the identified medical system. When the auxiliary device is communicatively paired with the medical system the auxiliary device may be configured to exchange data with the medical system. Thus, the auxiliary device or a user of the auxiliary device may have access to one or more functional features associated with the medical system. For example, the user may, by way of an auxiliary device, view content (e.g., an endoscopic video stream, patient information, surgical team information, etc.) associated with the medical system, interact with the medical system (e.g., control one or more features or settings of the medical system), view information (e.g., patient information, surgical team information, etc.) about a medical procedure being performed with the medical system (e.g., a surgical session performed with surgical system 100), and/or communicate with other users by way of additional user devices that are communicatively paired with the medical system. As another example, a user control system for a proctor surgeon may, upon successful pairing with manipulating system 102, be configured to control and interact with a manipulating system 102 that is primarily controlled by a primary user control system 104.

Pairing system 700 may communicatively pair the auxiliary device with the medical system in any suitable way. For example, pairing system 700 may establish a direct (e.g., peer-to-peer, single hop, or ad hoc) communication link between the auxiliary device and the medical system. The direct communication link may include, for example, a direct wireless connection, such as a Bluetooth connection, a near field communication connection, a Wi-Fi connection, a Wi-Fi Direct connection, a smartphone ad hoc network (SPAN) connection, a mobile device ad hoc network (MANET) connection, etc. Alternatively, pairing system 700 may establish an indirect communication link between the auxiliary device and the medical system by way of a remote computing system (e.g., remote computing system 802). The indirect communication link may include, for example, a wireless connection, such as by way of a network (e.g., network 804) and a remote computing system (e.g., remote computing system 802).

In some embodiments, pairing of the auxiliary device with the medical system may be conditioned on authentication of a user associated with the auxiliary device. For example, a pairing process may not be complete until the user of the auxiliary device has logged in to the auxiliary device or to an application or service provided by pairing system 700 and accessible through the auxiliary device. Additionally or alternatively, successful pairing may further be conditioned on other parameters, such as an identity of the authenticated user matching an identity of a surgical team member previously assigned to a surgical session (e.g., at initiation or creation of the surgical session), or upon the authenticated user successfully providing user input to identify, for example, a surgical session associated with the medical system with which the auxiliary device is attempting to pair (e.g., by identifying surgical session ID information, etc.). Pairing system 700 may detect such successful authentication in any suitable manner (e.g., by receiving data representative of the successful authentication from the medical system and/or the auxiliary device).

Figure 10:
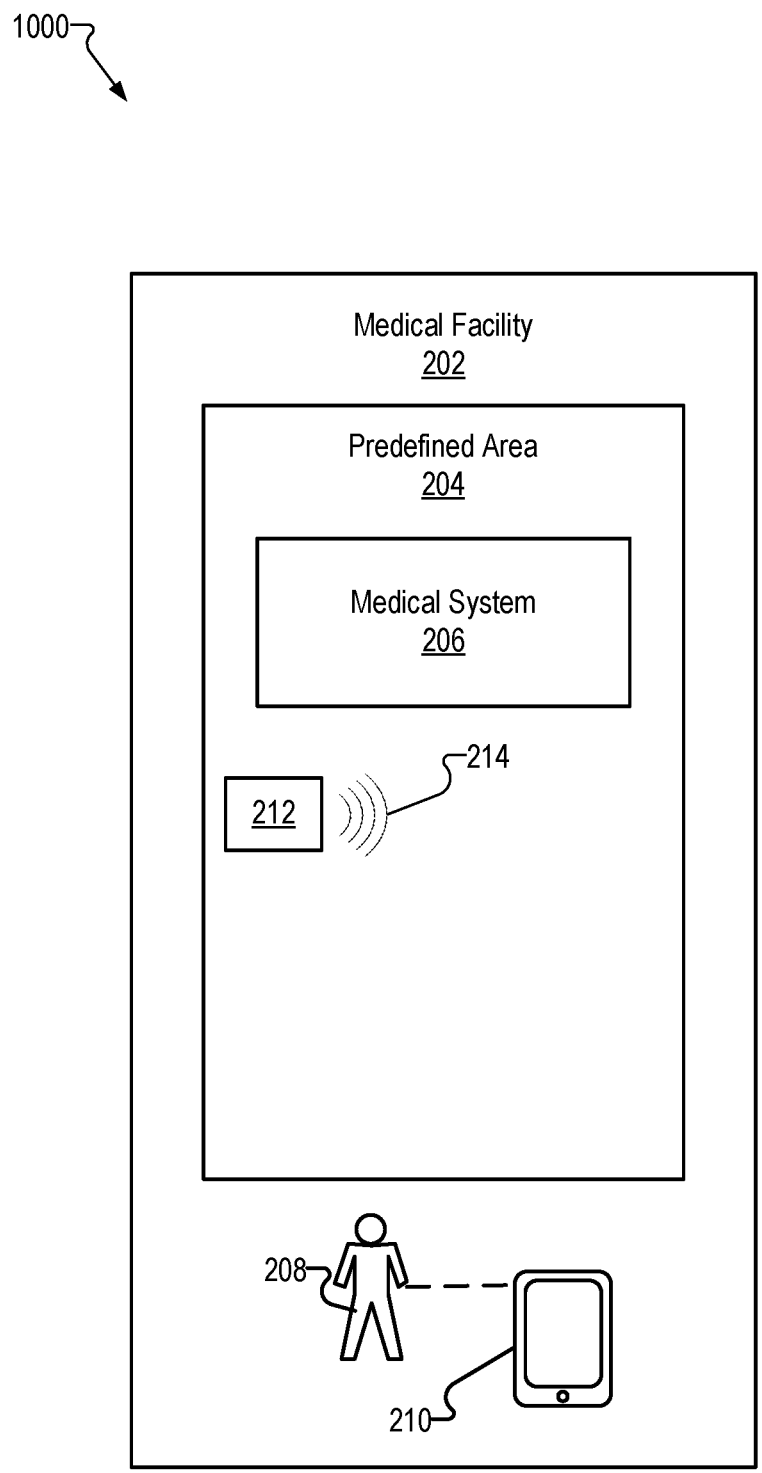
FIG. 10 illustrates another exemplary configuration of a medical facility including a beacon generator located within a predefined area according to principles described herein.

An exemplary pairing of an auxiliary device with a medical system will now be described with reference to the drawings. FIG. 10 shows another exemplary configuration 1000 of medical facility 202 in which user 208 (e.g., surgeon 110-1) and user device 210 (e.g., a tablet computer) are physically located outside of predefined area 204 (e.g., an operating room). As a result, user device 210 is out of the range of ultrasonic beacon 214 and therefore does not detect ultrasonic beacon 214. After user 208 and user device 210 have moved into predefined area 204, as shown in FIG. 2, such as to perform a medical procedure (e.g., a minimally invasive surgical procedure) with medical system 206 (e.g., surgical system 100), user device 210 is physically proximate to beacon generator 212 such that it detects ultrasonic beacon 214. Pairing system 700 may determine that user device 210 detects ultrasonic beacon 214 and, in response, identify a medical system associated with ultrasonic beacon 214. For example, pairing system 700 may determine, based on identification information included in ultrasonic beacon 214 (e.g., a location identifier, a medical system identifier, a beacon generator identifier, a medical session identifier, etc.), that medical system 206 is associated with ultrasonic beacon 214. Accordingly, pairing system 700 may communicatively pair user device 218 with medical system 206.

Certain foregoing embodiments have described pairing an auxiliary device with a medical system based on a single detected ultrasonic beacon. In other embodiments, pairing system 700 may be configured to pair an auxiliary device with a medical system based on detection of multiple ultrasonic beacons. As described above and as shown in FIGS. 4 and 5, medical facility 202 may include multiple beacon generators 212 within predefined area 204 and/or included in medical system 206, and, as shown in FIG. 6, medical facility 202 may include additional beacon generators 612 located outside of predefined area 204 (e.g., within predefined area 604).

In some examples pairing system 700 is configured to pair an auxiliary device with a medical system only if pairing system 700 determines that the auxiliary device detects a set of multiple ultrasonic beacons associated with a particular medical system. For instance, with reference to FIGS. 4-6, pairing system 700 may communicatively pair user device 210 with medical system 206 only if pairing system 700 determines that user device 210 detects any two or more of ultrasonic beacons 214-1 through 214-3.

In some examples pairing system 700 is configured to pair an auxiliary device with a medical system only if pairing system 700 determines that the auxiliary device detects the set of all ultrasonic beacons associated with the medical system. For instance, pairing system 700 may communicatively pair user device 210 with medical system 206 only if pairing system 700 determines that user device 210 detects all ultrasonic beacons 214 (e.g., ultrasonic beacons 214-1 through 214-3) associated with medical system 206. If pairing system 700 determines that user device 210 does not detect all ultrasonic beacons 214 associated with medical system 206, pairing system 700 does not communicatively pair user device 210 with medical system 206.

In some examples the set of ultrasonic beacons comprises all ultrasonic beacons included in components of the medical system. For instance, the set of ultrasonic beacons may include a unique component identifier for each component included in the medical system. In this way pairing system 700 does not pair the auxiliary device with the medical system unless pairing system 700 determines that the auxiliary device has detected an ultrasonic beacon associated with each component of the medical system (e.g., an ultrasonic beacon included in manipulating system 102, an ultrasonic beacon included in user control system 104, and an ultrasonic beacon included in auxiliary system 106).

Pairing system 700 may determine whether an auxiliary device detects a set of all ultrasonic beacons associated with a medical system in any suitable way. For example, pairing system 700 may refer to medical facility data (e.g., association table 900) to determine whether the auxiliary device detects all ultrasonic beacons associated with a particular medical system.

In some examples, pairing system 700 may condition pairing of an auxiliary device with a medical system on a determination that the auxiliary device does not detect any ultrasonic beacons associated with another medical system. For instance, as shown with reference to FIG. 6, pairing system 700 may communicatively pair user device 210 with medical system 206 only if pairing system 700 determines that user device 210 does not detect any ultrasonic beacons other than ultrasonic beacons 214 (e.g., any of ultrasonic beacons 614-1 through 614-3). If pairing system 700 determines that user device 210 detects any ultrasonic beacon 614, pairing system 700 does not communicatively pair user device 210 with medical system 206, even if user device 210 detects one or more (or all) ultrasonic beacons 214.

Figure 11:
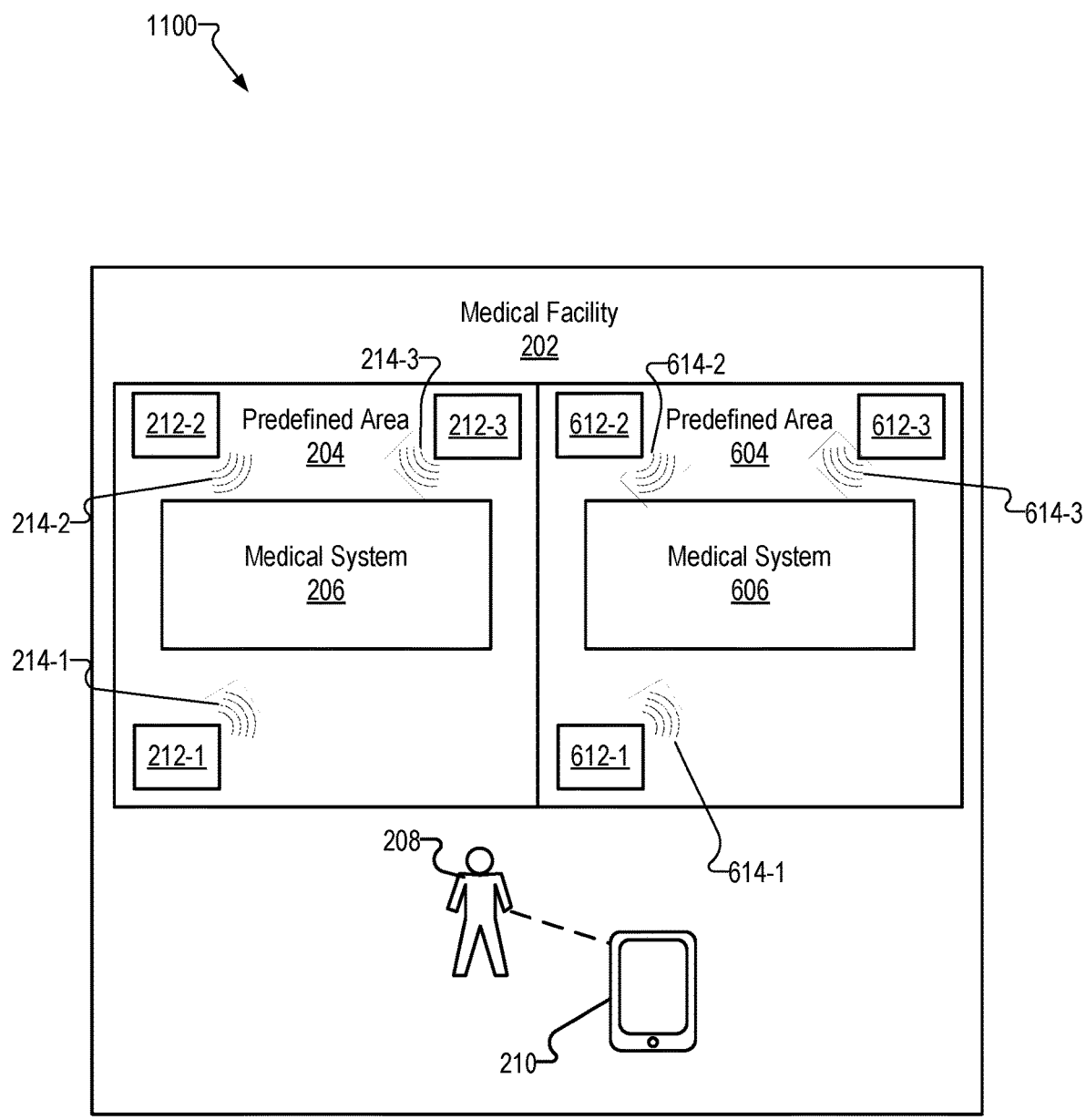
FIG. 11 illustrates another exemplary configuration of a medical facility including multiple beacon generators located within multiple predefined areas according to principles described herein.

An exemplary pairing of an auxiliary device with a medical system based on a detection of all ultrasonic beacons associated with the medical system will now be described with reference to the drawings. FIG. 11 shows another exemplary configuration 1100 of medical facility 202 in which user 208 (e.g., surgeon 110-1) and user device 210 (e.g., a tablet computer) are physically located outside of predefined areas 204 and 604. As a result, user device 210 is out of the range of ultrasonic beacons 214 and 614 and therefore does not detect ultrasonic beacons 214 and 614. After user 208 and user device 210 have moved into predefined area 204, as shown in FIG. 6, such as to perform a medical procedure (e.g., a minimally invasive surgical procedure) with medical system 206 (e.g., surgical system 100), user device 210 is physically proximate to beacon generators 212 such that user device 210 detects ultrasonic beacons 214. However, user device 210 is also physically proximate to beacon generators 612 such that user device 210 detects stray ultrasonic beacons 614-1 and 614-2 from predefined area 604. However, user device 210 is not physically proximate to beacon generator 612-3 and thus does not detect ultrasonic beacon 614-3.

Pairing system 700 may access or refer to association table 900 and determine, based on a comparison of unique identification information (e.g., beacon generator IDs) included in ultrasonic beacons 214 with association table 900, that ultrasonic beacons 214 are all associated with the medical system having a medical system ID "DV002," and that no other ultrasonic beacons are associated with medical system ID "DV002". Pairing system 700 may also determine, based on a comparison of unique identification information (e.g., beacon generator IDs) included in ultrasonic beacons 614-1 and 614-2, that ultrasonic beacons 614-1 and 614-2 are associated with the medical system having a medical system ID "DV003." However, pairing system 700 may further determine from association table 900 that user device 210 has not detected all ultrasonic beacons associated with the medical system having the medical system ID "DV003," (e.g., has not detected ultrasonic beacon "BG007" associated with medical system ID "DV003"). Accordingly, pairing system 700 may determine that user device 210 is located within predefined area 204 and/or physically proximate to medical system 206 and, in response, communicatively pair user device 210 with medical system 206. In this example detection of stray ultrasonic beacons 614-1 and 614-2 does not result in pairing of user device 210 with medical system 606 or prevent the pairing of user device 210 with medical system 206.

In additional or alternative examples, pairing system 700 may pair an auxiliary device with a medical system that is associated with the most ultrasonic beacons detected by the auxiliary device. For example, pairing system 700 may pair user device 210 with medical system 206 in response to determining that user device 210 detects three ultrasonic beacons (e.g., ultrasonic beacons 214-1 through 214-3) associated with medical system 206 and detects only two ultrasonic beacons (e.g., ultrasonic beacons 614-1 and 614-2) associated with medical system 606.

Additionally or alternatively, pairing system 700 may pair an auxiliary device with a medical system based on a signal strength of the detected ultrasonic beacons. For example, pairing system 700 may pair an auxiliary device with a medical system only if the signal strengths of the ultrasonic beacons associated with the medical system exceed a predetermined threshold.

Figure 12:
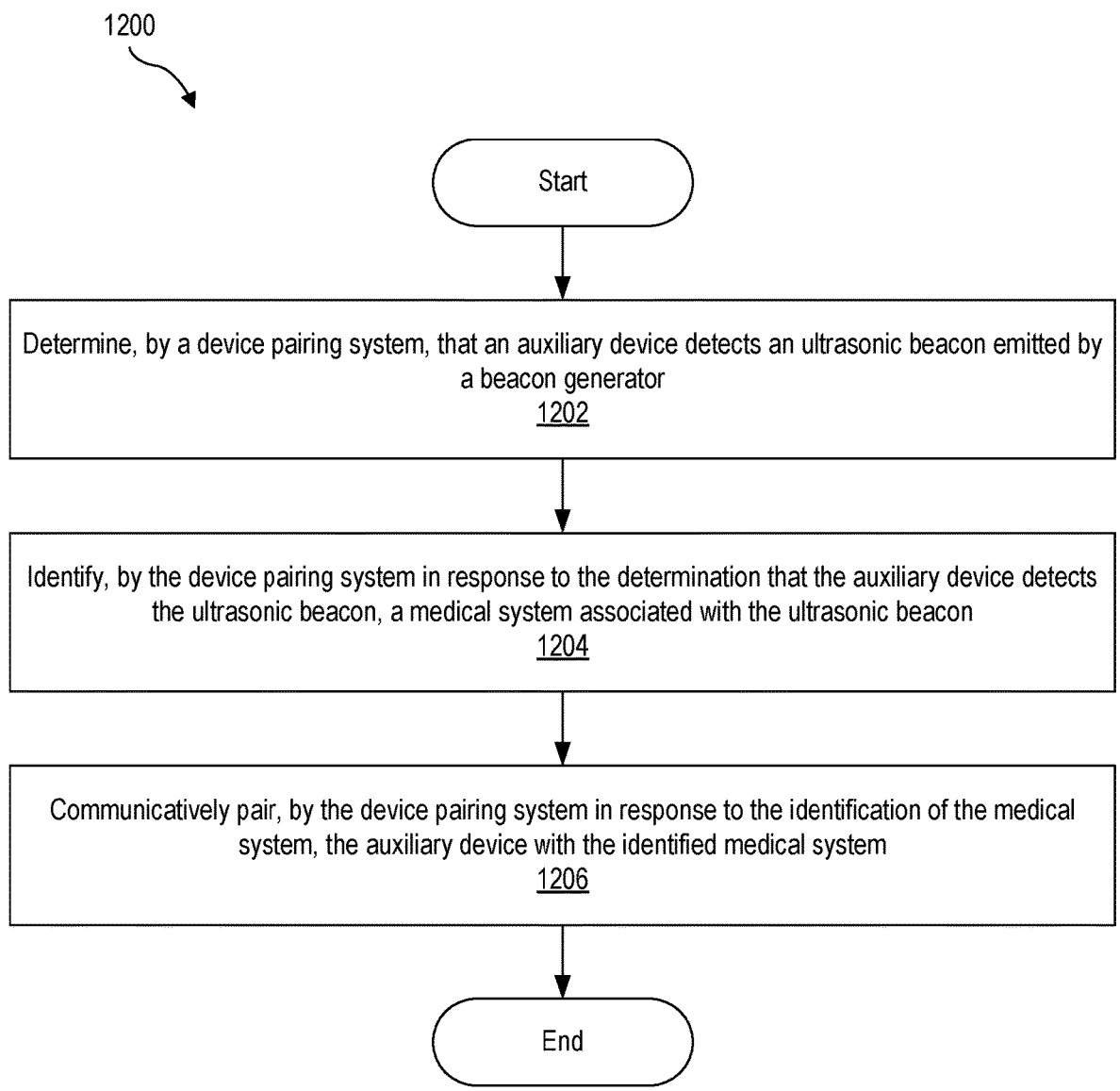
FIGS. 12 and 13 illustrate exemplary methods of communicatively pairing an auxiliary device with a medical system according to principles described herein.

FIG. 12 shows an exemplary method 1200 of communicatively pairing an auxiliary device with a medical system. While FIG. 12 illustrates exemplary operations according to one embodiment, other embodiments may omit, add to, reorder, combine, and/or modify any of the steps shown in FIG. 12 One or more of the operations shown in in FIG. 12 may be performed by pairing system 700, any components included therein, and/or any implementation thereof.

In operation 1202, a device pairing system determines that an auxiliary device detects an ultrasonic beacon emitted by a beacon generator. Operation 1202 may be performed in any of the ways described herein.

In operation 1204, the device pairing system identifies, in response to the determination that the auxiliary device detects the ultrasonic beacon, a medical system associated with the ultrasonic beacon. Operation 1204 may be performed in any of the ways described herein.

Figure 13:
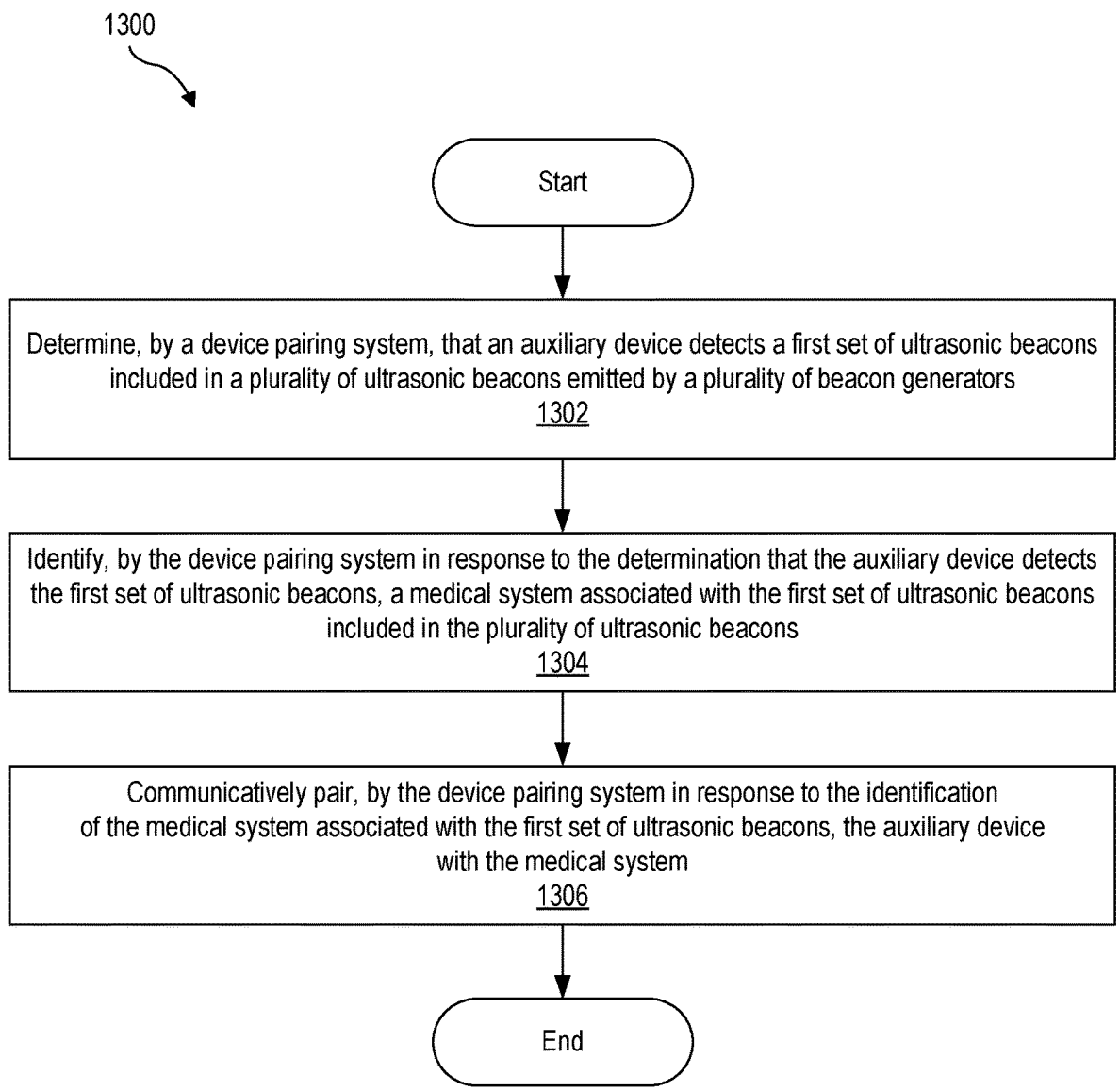

In operation 1206, the device pairing system communicatively pairs, in response to the identification of the medical system, the auxiliary device with the identified medical system. Operation 1206 may be performed in any of the ways described herein, FIG. 13 shows another exemplary method 1300 of communicatively pairing an auxiliary device with a medical system. While FIG. 13 illustrates exemplary operations according to one embodiment, other embodiments may omit, add to, reorder, combine, and/or modify any of the steps shown in FIG. 13 One or more of the operations shown in in FIG. 13 may be performed by pairing system 700, any components included therein, and/or any implementation thereof.

In operation 1302, a device pairing system determines that an auxiliary device detects a first set of ultrasonic beacons included in a plurality of ultrasonic beacons emitted by a plurality of beacon generators. Operation 1302 may be performed in any of the ways described herein.

In operation 1304, the device pairing system identifies, in response to the determination that the auxiliary device detects the first set of ultrasonic beacons, a medical system associated with the first set of ultrasonic beacons included in the plurality of ultrasonic beacons. Operation 1304 may be performed in any of the ways described herein.

In operation 1306, the device pairing system communicatively pairs, in response to the identification of the medical system associated with the first set of ultrasonic beacons, the auxiliary device with the medical system. Operation 1306 may be performed in any of the ways described herein.

In addition to communicatively pairing a device with a medical system, as described above, pairing system 700 may also be configured to perform various operations associated with managing operations associated with a medical system and/or perform various operations associated with controlling communicative pairing of a device with a medical system. For example, pairing system 700 may determine that a device located within a predefined area within a medical facility detects one or more ultrasonic beacons emitted by one or more beacon generators associated with a medical system located within the predefined area. A beacon generator may be associated with the medical system in any suitable way. For example, a beacon generator may be included in one of the components of surgical system 100 (e.g., manipulating system 102, user control system 104, or auxiliary system 106). As another example, a beacon generator may be included in a mobile accessory cart included in the medical system (e.g., accessory cart 118). As yet another example, a beacon generator may be a standalone device (e.g., affixed to a wall of an operating room or otherwise separate from medical system 206) but configured to receive information about medical system 206 and include the information in an ultrasonic beacon emitted by the beacon generator.

The device may be any suitable device configured to detect an ultrasonic beacon. In some examples the device may be a component of a medical system. For instance, the device may be another one of the components of surgical system 100 (e.g., manipulating system 102, user control system 104, or auxiliary system 106). Thus, a first component of surgical system 100 may be configured to listen for and detect an ultrasonic beacon emitted by a beacon generator included in a second component of surgical system 100.

In alternative examples, the device may be a device that is not included in the medical system, such as a user device (e.g., user device 210), a mobile accessory cart, and the like. In some examples the device may be communicatively coupled with the medical system, such as when a user device is communicatively paired with the medical system. In other examples the device is not communicatively paired with the medical system.

Pairing system 700 may also be configured to decode each detected ultrasonic beacon to identify information included in each detected ultrasonic beacon. Pairing system 700 may identify information included in a detected ultrasonic beacon in any suitable way. For example, pairing system 700 may process and analyze audio signals representative of the detected ultrasonic beacon to identify information included in the detected ultrasonic beacon. In alternative examples the device (e.g., an application executed by the device) may identify the information included in the ultrasonic beacon (e.g., in any of the ways described herein) and transmit data representative of the information to pairing system 700, Pairing system 700 may identify the information included in the ultrasonic beacon based on the data representative of the information transmitted by the device to pairing system 700.

Pairing system 700 may use the information included in the detected one or more ultrasonic beacons to perform an operation associated with the medical system. The operation associated with the medical system may include any suitable operation that may be performed by pairing system 700 to control and/or manage medical system operations and/or device operations.

As used herein, medical system operations may include any mechanical, electrical, optical, hardware, and/or software-based operations performed by the medical system (or by a component of the medical system) as may serve a particular implementation. For example, medical system operations may include, without limitation, establishing a communicative connection (pairing) with another device (e.g., a user device), detecting an error, generating an error code, authenticating a user of the medical system, adjusting a pose of a component of the medical system (e.g., moving manipulator arms 112 and/or surgical instruments coupled to manipulator arms 112), operating a functional feature of the medical system (e.g., energizing a cautery instrument), adjusting a medical system setting, and the like.

As used herein, device operations may include any electrical, hardware, and/or software-based operations performed by a device associated with the medical system as may serve a particular implementation. A device may be associated with a medical system in any suitable way. For example, the device may be communicatively paired with the medical system, may be located in the same predefined area as the medical system, used (or approved for use) by a user of the medical system or a medical session associated with the medical system, assigned to a user or medical session associated with the medical system, etc. Device operations may include, without limitation, communicatively pairing the device with the medical system, authenticating a user of the device, providing the user with access to a functional feature of an application executed by the device, providing the user with access to a functional feature of the medical system by way of the device, presenting information by way of a graphical user interface on the device, and the like.

In some examples, pairing system 700 may perform an operation associated with the medical system by setting or specifying one or more rules for a medical system operation and/or a device operation. For example, components of a medical system may each be configured to listen for and detect ultrasonic beacons emitted by other components of the medical system. Pairing system 700 may use the information included in the detected ultrasonic beacons to set one or more rules associated with the medical system, such as rules for communicatively pairing a device with the medical system, rules for authenticating a user of the medical system, rules for changing an operational state of the medical system (e.g., setting an active control state, a standby state, a suspended state, an OFF state, etc.), and the like.

To illustrate with reference to FIG. 5, medical system 206 may be implemented by surgical system 100. Manipulating system 102 may include beacon generator 212-1 configured to emit ultrasonic beacon 214-1, user control system 104 may include beacon generator 212-2 configured to emit ultrasonic beacon 214-2, and auxiliary system 106 may include beacon generator 212-3 configured to emit ultrasonic beacon 214-3. Each ultrasonic beacon 214 may include a unique component ID of the corresponding component of surgical system 100. Pairing system 700 may determine that auxiliary system 106 detects ultrasonic beacons 214-1 and 214-2 emitted from manipulating system 102 and user control system 104, respectively. Pairing system 700 may determine, based on the information included in each of ultrasonic beacons 214-1 through 214-3, that manipulating system 102, user control system 104, and auxiliary system 106 are all located within the same area and/or located within predefined area 204. Accordingly, pairing system 700 may set rules for communicatively pairing user device 210 with medical system 206 based on the information included in ultrasonic beacons 214. The pairing criteria may require, for example, that user device 210 detect each of ultrasonic beacons 214-1 through 214-3 as a condition to the device pairing system communicatively pairing user device 210 with medical system 206.

Pairing system 700 may additionally or alternatively perform an operation associated with the medical system by determining, based on identification information included in a plurality of ultrasonic beacons detected by the device, that the device is located within the same predefined area as the medical system. In some examples pairing system 700 may also communicatively pair the device with the medical system in response to a determination that the device is located within the same predefined area as the medical system.

Pairing system 700 may determine that the device is located within the same predefined area as the medical system in any suitable way. In some examples, the device is determined to be located within the same predefined area as the medical system when a plurality of ultrasonic beacons detected by the device match a set of predefined rules. The rules may specify a set of ultrasonic beacons that must be detected, a signal strength of the ultrasonic beacons, timing for the detection of the ultrasonic beacons (e.g., specified time periods), etc. To illustrate with reference to FIG. 6, pairing system 700 may determine that user device 210 is located within predefined area 204 when user device 210 detects multiple ultrasonic beacons associated with the medical system (e.g., any two or more of ultrasonic beacons 214-1 through 214-3). This may be inferred by the fact that it is unlikely that user device 210 would detect multiple stray ultrasonic beacons (e.g., ultrasonic beacons 614-1 through 614-3) originating from a room or location where the device is not presently located (e.g., predefined area 604). In some examples pairing system 700 may determine that user device 210 is located within the same predefined area as medical system 206 only when user device 210 detects all ultrasonic beacons associated with medical system 206 (e.g.; ultrasonic beacons 214-1 through 214-3).

In additional or alternative examples, the device may be determined to be located within the same predefined area as the medical system based on identification information included in a primary ultrasonic beacon. To illustrate again with reference to FIG. 6, a plurality of ultrasonic beacons 214-1 through 214-3 detected by user device 210 may include a primary ultrasonic beacon (e.g., ultrasonic beacon 214-1) associated with a first component (e.g.; auxiliary system 104) included in a plurality of components of medical system 206 (e.g., surgical system 100) and one or more secondary beacons (e.g.; ultrasonic beacons 214-2 and 214-3) associated with one or more additional components (e.g., manipulating system 102 and/or user control system 104) included in the plurality of components of medical system 206. The primary beacon (ultrasonic beacon 214-1) may include (e.g., encode) identification information identifying each of the one or more additional components. Pairing system 700 may determine that user device 210 is located within the same predefined area 204 as medical system 206 if the identification information included in the one or more secondary beacons (ultrasonic beacons 214-2 and 214-3) detected by user device 210 matches the identification information included in the detected primary beacon (ultrasonic beacon 214-1). On the other hand, if pairing system 700 determines that the identification information included in the one or more secondary beacons (ultrasonic beacons 214-2 and 214-3) does not match the identification information included in the primary beacon (ultrasonic beacon 214-1), pairing system 700 does not determine that user device 210 is located within the same predefined area 204 as medical system 206 and may prohibit communicative pairing of user device 210 with medical system 206.

Pairing system 700 may configure the primary beacon to include the identification information identifying the one or more additional components of the medical system in any suitable way. In some examples, pairing system 700 may determine that the one or more additional components are communicatively connected to the first component. For example, the first component of the medical system (e.g., auxiliary system 106) may know, by way of an established wired or wireless communication link (e.g., control lines 116), the identity of one or more additional components (e.g., manipulating system 102 and/or user control system 104) communicatively connected with the first component. In response to the determination that the one or more additional components are communicatively connected to the first component, pairing system 700 may direct the beacon generator configured to emit the primary beacon to include the identification information identifying each of the one or more additional components in the primary beacon.

Alternatively, the first component (or a beacon generator associated with the first component), may detect one or more secondary ultrasonic beacons (e.g., ultrasonic beacons 214-2 and 214-3) associated with the one or more additional components communicatively connected with the first component. Pairing system 700 may determine that the first component (or the beacon generator associated with the first component) detects the one or more secondary ultrasonic beacons (ultrasonic beacons 214-2 and 214-3). In response, pairing system 700 may direct the beacon generator configured to emit the primary beacon (e.g., beacon generator 212-1) to include the identification information included in each of the one or more secondary beacons (ultrasonic beacons 214-2 and 214-3) in the primary beacon (ultrasonic beacon 214-1).

In some embodiments, a predefined area may include a standalone (e.g., room-specific) beacon generator configured to operate as a single source of information associated with a medical system. For example, the standalone beacon generator may be configured to detect all ultrasonic beacons emitted by medical system components and/or other devices that are present within a particular predefined area. Pairing system 700 may identify information (e.g., component IDs, etc.) included in the ultrasonic beacons and direct the standalone beacon generator to emit one or more ultrasonic beacons that includes information associated with all medical system components and/or other devices present within the predefined area. Thus, when a device detects the ultrasonic beacon from the standalone beacon generator, pairing system 700 may condition pairing of the device with the medical system on detection, by the device, of ultrasonic beacons from all medical system components and/or other devices identified in the ultrasonic beacon emitted by the standalone beacon generator.

In some scenarios ultrasonic beacons simultaneously emitted from different, non-connected sources may overlap with one another, thus making it difficult for a device to discriminate between different ultrasonic beacons detected by the device. Accordingly, pairing system 700 may be configured to coordinate the output from multiple beacon generators to prevent the emitted ultrasonic beacons from overlapping with one another. In some examples, pairing system 700 may coordinate or modify the output from multiple beacon generators based on information included in a detected ultrasonic beacon.

For example, a first device (e.g., a component of a medical system) may have a first beacon generator that emits a first ultrasonic beacon within a predefined area (e.g., an operating room). When a second device (e.g., a mobile accessory cart) having a second beacon generator that emits a second ultrasonic beacon detects the first ultrasonic beacon, pairing system 700 may determine that the second device detects the first ultrasonic beacon emitted from the first device (e.g., by the first beacon generator). In response, pairing system 700 may direct the second device (e.g., the second beacon generator) to modify the second ultrasonic beacon so as to not overlap or interfere (whether constructively or destructively) with the first ultrasonic beacon. Alternatively, pairing system 700 may direct the first device to modify the first ultrasonic beacon.

In some examples modification of the second ultrasonic beacon is conditioned on a determination that the second ultrasonic beacon overlaps with the first ultrasonic beacon. In these examples pairing system 700 may be configured to determine, in response to the determination that the second device detects the first ultrasonic beacon, whether the second ultrasonic beacon overlaps with the first ultrasonic beacon. This may be done in any suitable way. In some examples overlap may be conditioned on a determination that the first device detects the second ultrasonic beacon. If pairing system 700 determines that the second ultrasonic beacon overlaps with the first ultrasonic beacon, pairing system 700 may direct the second device to modify the second ultrasonic beacon. On the other hand, if pairing system 700 determines that the second ultrasonic beacon does not overlap with the first ultrasonic beacon, the pairing system 700 does not direct the second device to modify the second ultrasonic beacon.

The second ultrasonic beacon may be modified in any suitable way, such as by changing the configuration (e.g., a frequency, amplitude, waveform, etc.) of the second ultrasonic beacon, direct-sequence spread spectrum (DSSS) direct sequence code division multiple access (DS-CDMA), applying a back-off time, and the like. For example, if pairing system 700 determines that the second device detects the first ultrasonic beacon, pairing system 700 directs the second device to wait for a randomly selected period of time (the "backoff period"), which is counted down by a backoff counter, and then checks again to see if the second device detects the first ultrasonic beacon. If the second device does not detect the first ultrasonic beacon, pairing system 700 directs the second device to emit the second ultrasonic beacon. If pairing system 700 determines that the second device detects the first ultrasonic beacon when the backoff counter reaches zero, the backoff period is set again and the process is repeated.

In the foregoing embodiments pairing system 700 is configured to coordinate the output of ultrasonic beacons from beacon generators that are not communicatively connected to one another such that the ultrasonic beacons do not overlap or interfere with one another. In other examples in which beacon generators are communicatively connected to one another (e.g., beacon generators 212 included in medical system 206), a control system of the beacon generators (e.g., a control system of medical system 206) is configured to coordinate the output of the ultrasonic beacons (e.g., ultrasonic beacons 214) from the beacon generators such that the ultrasonic beacons do not overlap or interfere with one another.

As mentioned above, pairing system 700 may use the information included in a detected ultrasonic beacon to perform an operation associated with the medical system. In some examples pairing system 700 may use the information included in an ultrasonic beacon to identify an error and/or provide a notification of an error with the medical system. For example, when a component of a medical system detects an error, the component may be configured (by way of a beacon generator included in the component) to emit an ultrasonic beacon that includes information about the error. Pairing system 700 may use the information included in the ultrasonic beacon to perform an operation, such as direct the device (e.g., another component of the medical system, a user device, etc.) to present the information about the error.

To illustrate, consider again the example of FIG. 5 in which medical system 202 is implemented by surgical system 100. If a wired (e.g., a fiber optic) connection between manipulating system 102 and auxiliary system 106 is broken, beacon generator 212-1 included in manipulating system 102 may configure ultrasonic beacon 214-1 to include information indicating that the connection with auxiliary system 106 is broken (e.g., a fault code indicating a loss of a wired connection). When auxiliary system 106 detects ultrasonic beacon 214-1, pairing system 700 may direct auxiliary system 106 and/or manipulating system 102 to present a notification (e.g., a warning tone, a visual message, an indicator light, etc.) indicating that the wired connection between manipulating system 102 and auxiliary system 106 is broken. Additionally or alternatively, pairing system 700 may direct any other component of surgical system 100 (e.g., user control system 104) and/or a device communicatively paired with surgical system 100 to present the notification.

In some examples pairing system 700 may use the information included in the detected ultrasonic beacon to present inventory information of components included with the medical system (or with a component of the medical system). For example, the medical system may emit an ultrasonic beacon that identifies accessories (e.g., surgical instruments) included with the medical system. In some examples the ultrasonic beacon includes information (e.g., surgical instrument IDs) for all accessories included with the medical system. Alternatively, the ultrasonic beacon includes identification information (e.g., a mobile accessory cart ID) that may be used by pairing system 700 to access inventory information from a remote computing system (e.g., from a medical facility management system).

The inventory information may be generated in any suitable way. In some examples the medical system is configured to automatically detect components that are included with the medical system. For example, manipulating system 102 may be configured to automatically detect which surgical instruments are coupled to manipulator arms 112. As another example, a medical system may automatically detect accessories included with the medical system by way of a radio frequency identification (RFID) system. For instance, a mobile accessory cart may include an RFID reader configured to automatically detect an RFID tag attached to surgical instruments when the surgical instruments are placed on the mobile accessory cart. In further examples, the inventory information may be generated manually, such as by a user scanning a barcode attached to a surgical instrument, manually entering surgical instrument ID information, and the like.

The inventory information may be stored locally to the medical device and/or remotely on a remote computing system (e.g., a medical facility management system). Additionally, the inventory information included in the ultrasonic beacon and/or presented by the device may include additional information beyond the identity of the components included with the medical system. For example, the inventory information may include an intended location for the surgical instruments, one or more users who have permission to use and/or take the surgical instruments, instructions associated with the surgical instruments, etc.

Pairing system 700 may direct any suitable device to present the inventory information, such as a component of the medical system (e.g., manipulating system 102, user control system 104, or auxiliary system) or a user device (e.g., user device 210) that detects that the ultrasonic beacon.

An example will now be illustrated with reference to FIG. 2. In this example, medical system 206 is implemented by a mobile accessory cart that is used to carry various sterilized surgical instruments throughout medical facility 202 and distribute the surgical instruments to their intended locations. As shown, medical system 206 (the mobile accessory cart) includes beacon generator 212, which emits ultrasonic beacon 214 that includes inventory information identifying surgical instruments (not shown) that are carried by the mobile accessory cart.

When the mobile accessory cart enters predefined area 204 (e.g., an operating room), user device 210 detects ultrasonic beacon 214. Pairing system 700 identifies the inventory information included in ultrasonic beacon 214 and may direct user device 210 to present the inventory information (e.g., by way of an application executed by user device 210). Additionally or alternatively, pairing system 700 may direct surgical system 100 (e.g., manipulating system 102, user control system 104, and/or auxiliary system 106) to present the inventory information. The inventory information may specify, in addition to an identity of the instruments carried by the mobile accessory cart, which instruments are to remain in predefined area 204, which instruments are to be coupled with manipulating system 102, and which users are authorized to handle or operate each surgical instrument. The user may thereby readily ascertain which surgical instruments are on the mobile accessory cart and/or which surgical instruments the user should take from the cart for the operating room.

As another illustration, predefined area 204 may represent a sterile processing department room of a hospital, and medical system 206 may represent a mobile accessory cart carrying various surgical instruments. When user 208 (e.g., a technician) enters predefined area 204 with user device 210 to deliver surgical instruments to various operating rooms, user device 210 may detect ultrasonic beacon 214 emitted by the mobile accessory cart. Pairing system 700 may use inventory information included in ultrasonic beacon 214 to direct user device 210 to present the inventory information on user device 210. The inventory information presented on user device 210 may specify an intended destination of each surgical instrument carried by the mobile accessory cart.

Figure 14:
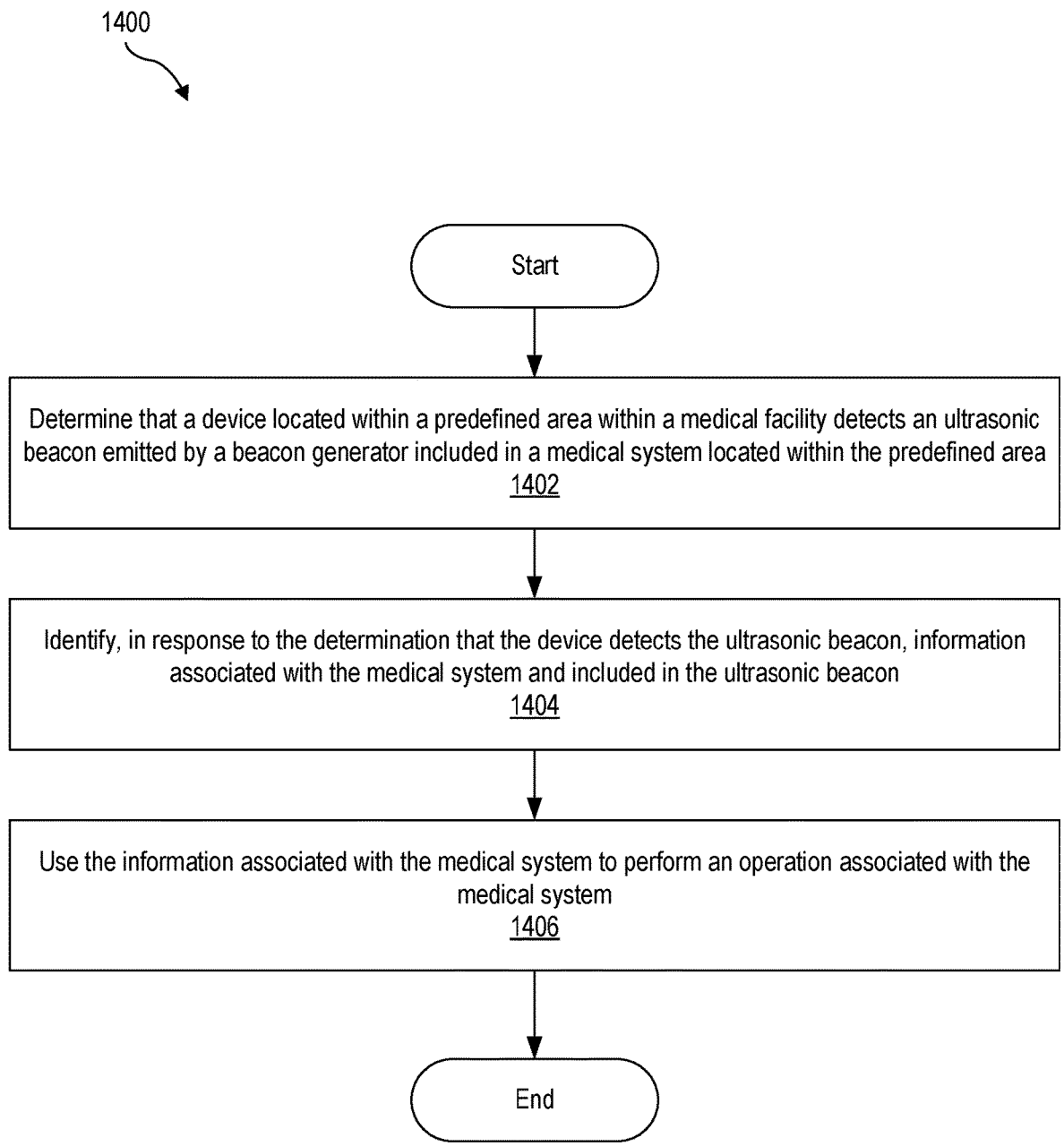
FIGS. 14 and 15 illustrate exemplary methods according to principles described herein.

FIG. 14 shows an exemplary method 1400. While FIG. 14 illustrates exemplary operations according to one embodiment, other embodiments may omit, add to, reorder, combine, and/or modify any of the steps shown in FIG. 14. One or more of the operations shown in in FIG. 14 may be performed by pairing system 700, any components included therein, and/or any implementation thereof.

In operation 1402, a pairing system determines that a device located within a predefined area within a medical facility detects an ultrasonic beacon emitted by a beacon generator included in a medical system located within the predefined area. Operation 1402 may be performed in any of the ways described herein.

In operation 1404, the pairing system identifies, in response to the determination that the device detects the ultrasonic beacon, information associated with the medical system and included in the ultrasonic beacon. Operation 1404 may be performed in any of the ways described herein.

In operation 1406, the pairing system uses the information associated with the medical system to perform an operation associated with the medical system. Operation 1406 may be performed in any of the ways described herein.

Figure 15:
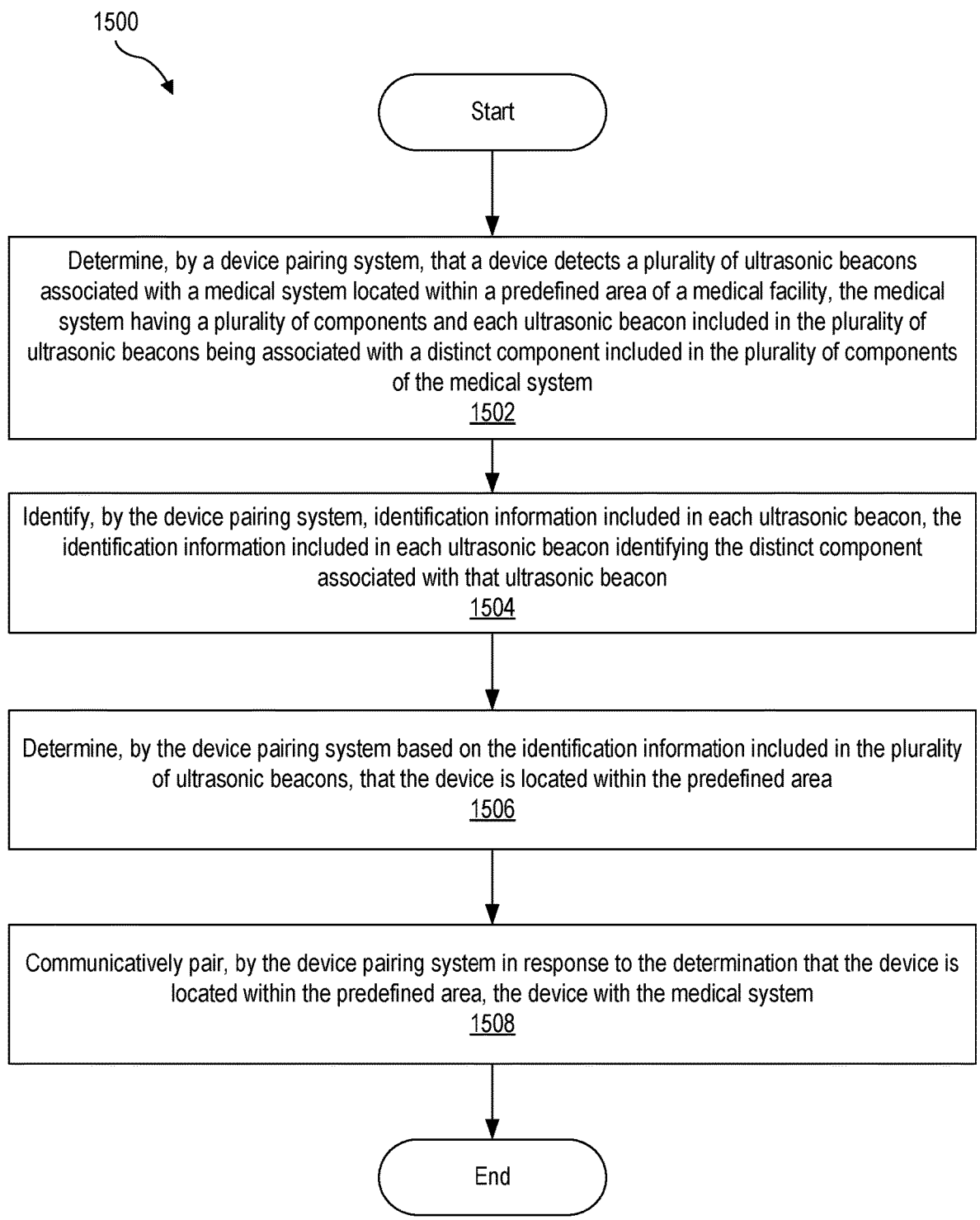

FIG. 15 shows another exemplary method 1500. While FIG. 15 illustrates exemplary operations according to one embodiment, other embodiments may omit, add to, reorder, combine, and/or modify any of the steps shown in FIG. 15. One or more of the operations shown in in FIG. 15 may be performed by pairing system 700, any components included therein, and/or any implementation thereof.

In operation 1502, a pairing system determines that a device detects a plurality of ultrasonic beacons associated with a medical system located within a predefined area of a medical facility, the medical system having a plurality of components and each ultrasonic beacon included in the plurality of ultrasonic beacons being associated with a distinct component included in the plurality of components of the medical system. Operation 1502 may be performed in any of the ways described herein.

In operation 1504, the pairing system identifies identification information included in each ultrasonic beacon, the identification information included in each ultrasonic beacon identifying the distinct component associated with that ultrasonic beacon. Operation 1504 may be performed in any of the ways described herein.

In operation 1506, the pairing system determines, based on the identification information included in the plurality of ultrasonic beacons, that the device is located within the predefined area. Operation 1506 may be performed in any of the ways described herein.

In operation 1508, the pairing system communicatively pairs, in response to the determination that the device is located within the predefined area, the device with the medical system. Operation 1508 may be performed in any of the ways described herein.

In the embodiments described above, the information included in the ultrasonic beacon may comprise identification information and, optionally, validation information and any other suitable information. In examples in which the information encoded in the ultrasonic beacon is large (e.g., 64 bits), a single channel communication scheme may be too slow due to the speed of sound and may result in the detection of echoes. Accordingly, in some examples the ultrasonic beacon may be transmitted in accordance with a multi-channel communication scheme. In the multi-channel communication scheme, the message is broken down into a plurality of subparts, and each message subpart is transmitted on its own channel.

Figure 16:
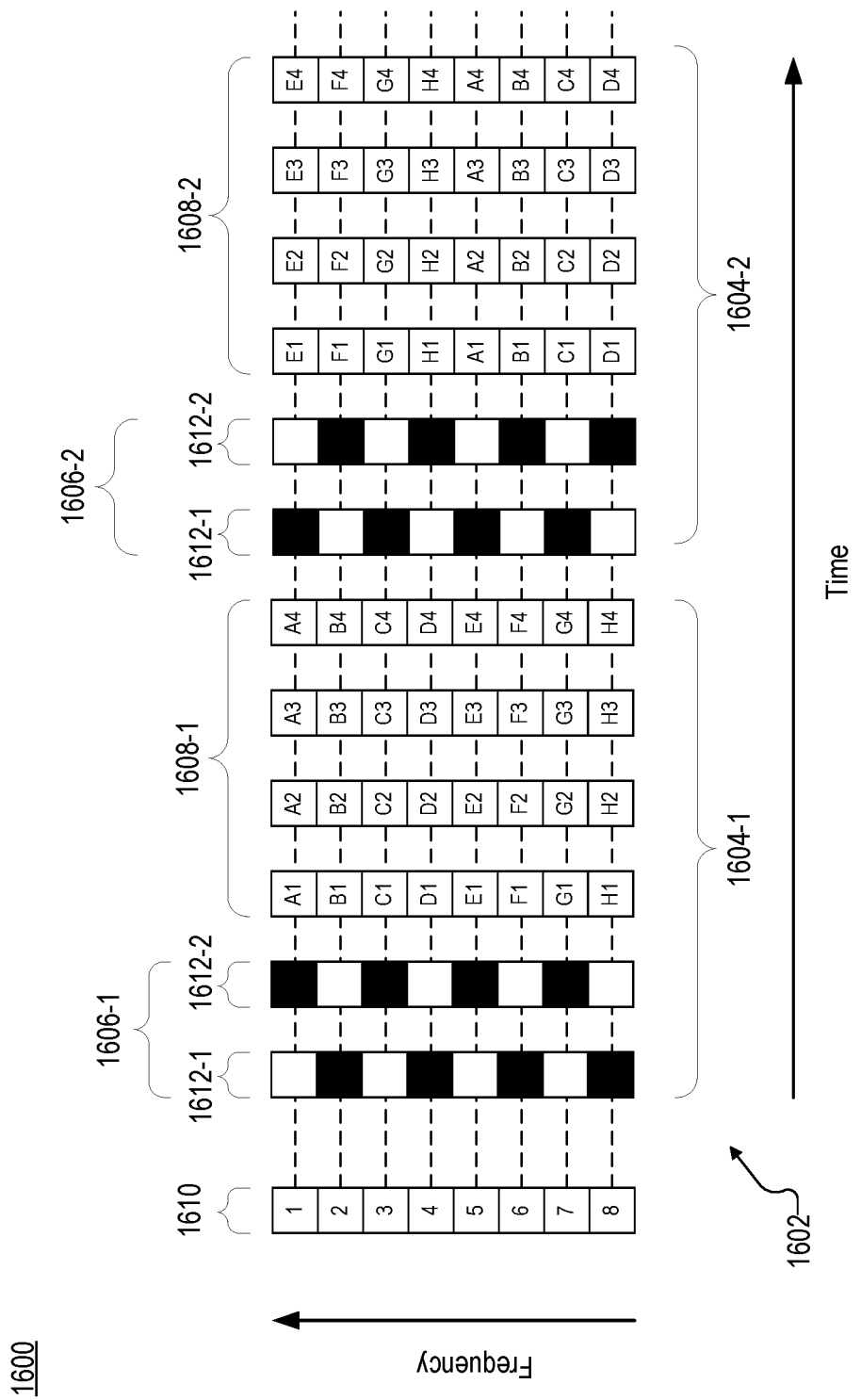
FIGS. 16 and 17 illustrate exemplary implementations of a multi-channel communication scheme for an ultrasonic beacon according to principles described herein.

FIG. 16 illustrates an exemplary configuration 1600 of a multi-channel communication scheme for an ultrasonic beacon 1602 ("beacon 1602"). FIG. 16 shows a first transmission 1604-1 of beacon 1602 and a second transmission 1604-2 of beacon 1602. Second transmission 1604-2 directly (e.g., without any intervening transmission) follows first transmission 1604-1. For ease of discussion FIG. 16 shows two transmissions, but beacon 1602 may have any other suitable number of transmissions. Transmissions 1604 may be repeated continuously until beacon 1602 is terminated (e.g., the beacon generator is turned off). For example, a third transmission identical to first transmission 1604-1 may follow second transmission 1604-2, a fourth transmission identical to second transmission 1604-2 may follow the third transmission, and so on. Beacon 1602 may be transmitted with any suitable frequency (e.g., time between successive pilot signals 1606), such as 100 Hz, 10 Hz, 1 Hz, etc.

Transmissions 1604-1 and 1604-2 of beacon 1602 include a pilot signal 1606-1 and a pilot signal 1606-2, respectively, and a message signal 1608-1 and a message signal 1608-2, respectively. Pilot signals 1606 and message signals 1608 are transmitted on a plurality of subchannels 1610 (e.g., subchannels 1610-1 to 1610-8). For ease of discussion FIG. 16 shows that beacon 1602 is transmitted on eight different subchannels 1610, but beacon 1602 may be transmitted on any other number of subchannels as may serve a particular implementation (e.g., 2, 4, 10, 16, 20, 32, 64, etc.). Subchannels 1610 may be within the ultrasonic range. In some examples, the bandwidth of the plurality of subchannels 1610 is within about 17.5 kHz to about 20 kHz. However, the plurality of subchannels 1610 may have any other suitable range as may serve a particular implementation.

In some examples, pilot signals 1606 and message signals 1608 are encoded in accordance with ON-OFF Keying (OOK). Accordingly, each bit is represented by the transmission of a particular frequency for a set period of time or the absence of transmission of a particular frequency for a set period of time. In alternative examples, pilot signals 1606 and message signals 1608 may be encoded with any other suitable encoding scheme, such as PSK, FSK, QAM, etc.

Pilot signals 1606 are configured to provide information for synchronization of transmissions 1604 and/or for estimation of characteristics of subchannels 1610 (e.g., signal-to-noise ratio of subchannels 1610, permutation of subchannels 1610, etc.). To this end, each pilot signal 1606 includes a first set of signals 1612-1 ("first set 1612-1") transmitted on subchannels 1610 followed by a second set of signals 1612-2 ("second set 1612-2") transmitted on subchannels 1610. Second set 1612-2 is the inverse of first set 1612-1 (e.g., a subchannel that transmits an ON signal (represented by a white box) in first set 1612-1 transmits an OFF signal (represented by a black box) in second set 1612-2, and vice versa). As a result, the switch from first set 1612-1 to second set 1612-2 produces a strong edge that is easily detectable. This sharp edge, when detected by a device, indicates the start of each transmission 1604 and thus facilitates synchronization of transmissions 1604. While pilot signals 1606 are shown and described as having two sets of signals, pilot signals 1606 may have more or fewer sets of signals. In some examples, each pilot signal 1606 may comprise a more compact signal for providing synchronization information and permutation information (described below).

First set 1612-1 and second set 1612-2 may have any suitable signal pattern as may serve a particular implementation. As shown in FIG. 16, first set 1612-1 and second set 1612-2 each comprise an alternating pattern of ON/OFF signals. However, sets 1612 are not limited to this configuration, and may have any other suitable configurations. In some examples, first set 1612-1 and second set 1612-2 may have a unique pattern configured to convey other information, such as a permutation order, as will be explained below in more detail.

Message signals 1608 are configured to transmit information such as identification information and/or validation information. The information encoded in message signal 1608 is divided into multiple subparts, and each subpart may include one or more bits. For ease of discussion, FIG. 16 shows that each message signal 1608 is divided into eight subparts denoted A through H, and each message subpart is transmitted in a single subchannel in four successive ON or OFF signals. For example, message subpart A of first transmission 1604-1 is transmitted on subchannel 1610-1 as signal A1, followed by signal A2, followed by signal A3, followed by signal A4. Message subparts B through H are transmitted on subchannels 1610-2 to 1610-8, respectively, in a similar manner. It will be recognized that each message signal 1608 may be divided into any suitable number of subparts (e.g., 2, 4, 10, 16, 20, 32, 64, etc.), and each message subpart may be transmitted as any one or more number of signals as may serve a particular implementation.

When a device detects first transmission 1604-1, the device may decode message signal 1608-1 by assembling each message subpart (e.g., signals A1 to A4), and then assembling message subparts A to H to produce the complete message information. In this way, the multi-channel communication scheme shown in FIG. 16 may transmit, by ultrasonic beacon 1602, a 10-digit number (represented by 32 bits) in a relatively short amount of time.

However, the multi-channel communication scheme illustrated in FIG. 16 is susceptible to dropout of one or more subchannels 1610. For example, the signal transmitted on one or more subchannels 1610 may be poor or corrupt due to ambient noise (e.g., noise in an operating room). If any one or more subparts of message signal 1608 are undetectable, undecodable, or otherwise corrupted, the complete message information may not be able to be decoded. As a result, the detecting device may not communicatively pair with a medical system associated with ultrasonic beacon 1602 or perform any of the other operations described herein.

To address this problem, the beacon generator that emits ultrasonic beacon 1602 may perform subchannel cycling of ultrasonic beacon 1602. In subchannel cycling, the beacon generator permutes the message subparts that are transmitted on subchannels 1610 for each successive transmission 1604 of beacon 1602. The beacon generator may permute the message subparts in any suitable way. In some examples, the message subparts are shifted on subchannels 1610 by one-half (½) of the total bandwidth of the spectrum of subchannels 1610. For example, as shown in FIG. 16 message subpart A is transmitted on subchannel 1610-1 in first transmission 1604-1 and is shifted to subchannel 1610-5 in second transmission 1604-2. Similarly, message subparts B, C, and D are shifted from subchannels 2, 3, and 4 in first transmission 1604-1 to subchannels 6, 7, and 8 in second transmission 1604-2, respectively. Message subparts E to H are shifted from subchannels 5 to 8 in first transmission 1604-1 to subchannels 1-4 in second transmission 1604-2, respectively. First and second transmissions 1604 may then be repeated indefinitely or until terminated.

With subchannel cycling, even if half of the subchannels 1610 (e.g., subchannels 1610-1 to 1610-4) are poor or corrupted in a first transmission 1604-1, the message information may be reconstructed by combining the detection result of first transmission 1604-1 and second transmission 1604-2. To reconstruct the message information from multiple transmissions 1604, the device needs to know or determine the permutation of the message subparts in each message signal. In some examples, each pilot signal 1606 is configured to encode permutation information for the corresponding message signal 1608, and the device may be configured to determine the permutation by decoding the pilot signal.

The encoded permutation information may have any suitable number of bits. Because there are only two different permutations when message subparts A to H are shifted by half the total subchannel spectrum, as shown in FIG. 16, there are two different permutations of pilot signals 1606. For example, pilot signal 1606-1 encodes permutation information for message signal 1608-1 and pilot signal 1606-2 encodes permutation information for message signal 1608-2. As shown in FIG. 16, pilot signal 1606-2 is the inverse of pilot signal 1606-1. However, pilot signal 1606-2 may take any other form and need not be the inverse of pilot signal 1606-1, so long as pilot signal 1606-2 is different from pilot signal 1606-1.

In some examples, the permutation information may comprise a single-bit signal transmitted on each channel. For example, as shown in FIG. 16, an ON signal on the odd-numbered subchannels and an OFF signal on the even numbered subchannels 1610 in first set 1612-1 may represent a first permutation (e.g., no shift, as shown in first transmission 1604-1), and an OFF signal on the odd-numbered subchannels 1610 and an ON signal on the even numbered subchannels in first set 1612-1 may indicate a second permutation (e.g., shifted by one-half the spectrum, as shown in second transmission 1604-2). In this way, pilot signals 1606 convey permutation information on each subchannel 1610. In alternative examples, the permutation information may be encoded in two bits in each subchannel 1610 (e.g., the combination of signals in first set 1612-1 and second set 1612-2 for each subchannel 1610). In additional or alternative examples, the permutation information may be encoded in two or more bits in two or more subchannels 1610 (e.g., the combination of signals in adjacent subchannels in first set 1612-1 and/or second set 1612-2). Such examples may not be quite as robust against subchannel dropout as single-bit permutation information transmitted on each subchannel 1610, but may enable use of more than two different permutations of message subparts, as will be described below with reference to FIG. 17. In yet further examples, the pilot signal may include one or more additional sets (in addition to sets 1612-1 and 1612-2) to convey permutation information and/or any other suitable information. In other examples, the permutation information may be encoded in each message signal 1608.

Figure 17:
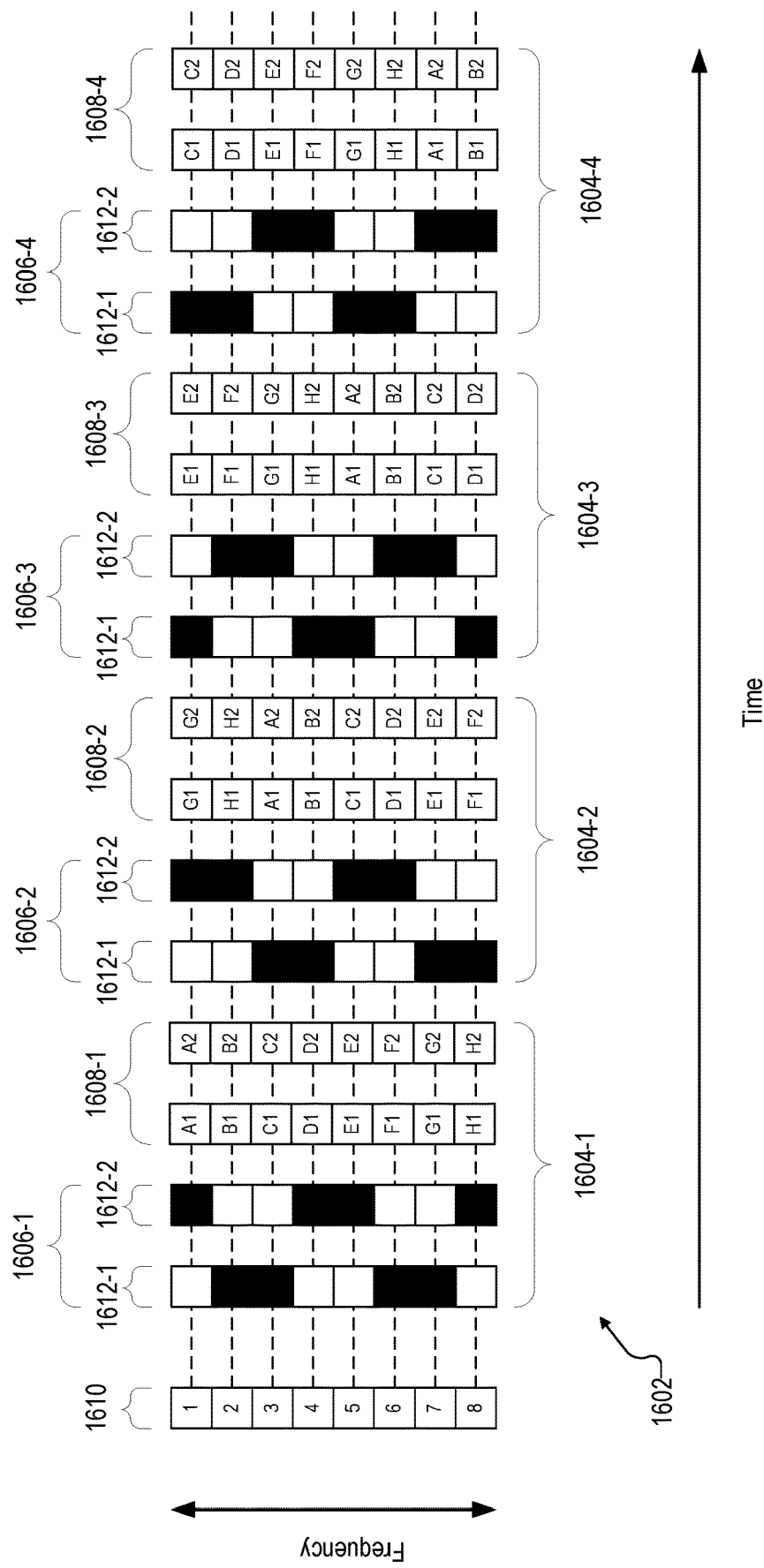

FIG. 17 illustrates an alternative configuration 1700 in which subchannel cycling is performed with more than two permutations of message subparts. FIG. 17 is similar to FIG. 16 except that FIG. 17 shows a third transmission 1604-3 comprising a pilot signal 1606-3 and a message signal 1608-3, and a fourth transmission 1604-4 comprising a pilot signal 1606-4 and a message signal 1608-4. For ease of discussion FIG. 17 shows that message signals 1608 include only two bits rather than four bits as shown in FIG. 16. However, message signals 1608 in FIG. 17 may include any number of bits as may serve a particular implementation.

As shown in FIG. 17, message subparts A to H are shifted by one-fourth (¼) of the total subchannel spectrum. For example, message subpart A is transmitted on subchannel 1610-1 in first transmission 1604-1, is transmitted on subchannel 1610-3 in second transmission 1604-2, is transmitted on subchannel 1610-5 in third transmission 1604-3, and is transmitted on subchannel 1610-7 in fourth transmission 1604-4. Similarly, message subparts B to H are shifted by two subchannels in each successive transmission 1604. Transmissions 1604-1 to 1604-4 may then be repeated indefinitely or until terminated.

Each pilot signal 1606 is unique and encodes the permutation for the message subparts of the corresponding message signal 1608. Thus, as shown in FIG. 17 there are four unique pilot signals 1606. The particular pilot signal permutations illustrated in FIG. 17 are only illustrative and are not limiting. The encoded permutation information may comprise any number of bits of pilot signals 1606. In some examples, the encoded permutation information comprises two bits (e.g., adjacent bits in first set 1612-1 or adjacent bits in second set 1612-2, or both bits in each subchannel 1610). Thus, each pilot signal 1606 transmits, on the eight subchannels 1610, the encoded permutation four times, thereby providing robustness against dropout of subchannels 1610.

In some examples, the permutation of the message subparts is not fixed, but may be adjusted dynamically. For example, pairing system 700 may determine (e.g., by way of a microphone or ultrasonic sensor) that background noise in the predefined area exceeds a threshold level. In response, pairing system 700 may direct the beacon generator to adjust the permutation of message subparts from a one-half shift to a one-fourth shift and correspondingly adjust the permutation information encoded in pilot signals 1606. Similarly, pairing system 700 may determine that background noise in the predefined area has dropped below a threshold level. In response, pairing system 700 may direct the beacon generator to adjust the permutation of message subparts from a one-fourth shift to a one-half shift and correspondingly adjust the permutation information encoded in pilot signals 1606. In some examples, pairing system 700 may apply an upper and/or lower background noise threshold to each distinct permutation (e.g., one-half shift, one-fourth shift, one-eighth shift, etc.).

In the examples described above, when a detected message signal 1608 is invalid (e.g., undetectable, corrupted, or not a valid message), the device may reconstruct the message information from multiple different transmissions 1604 of beacon 1602. In some examples, each message signal 1608 may encode, in addition to identification information, validation information that may be used by a detecting device to determine whether a detected message signal 1608 is valid or invalid. The validation information may include, for example, an error-correcting code, a checksum, or any other suitable validation information.

Figure 18:
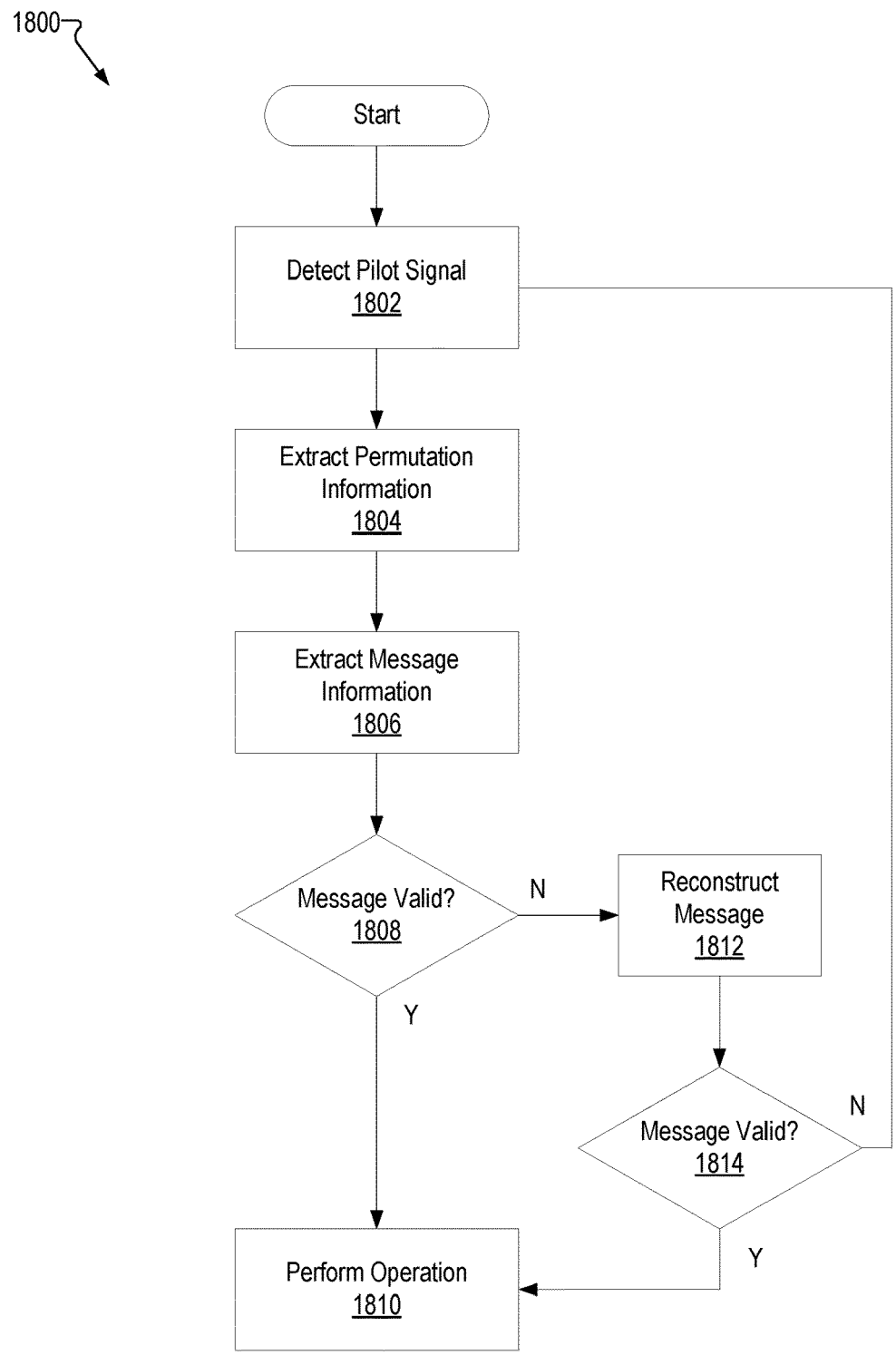
FIG. 18 illustrates an exemplary method of detecting an ultrasonic beacon and using information included in the ultrasonic beacon.

Detection of an ultrasonic beacon and use of identification of information encoded in the ultrasonic beacon will now be described with reference to FIG. 18. FIG. 18 shows an exemplary method 1800. While FIG. 18 illustrates exemplary operations according to one embodiment, other embodiments may omit, add to, reorder, combine, and/or modify any of the steps shown in FIG. 18. One or more of the operations shown in FIG. 18 may be performed by a device (e.g., an auxiliary device, a user device, a component of a medical system, an accessory cart, etc.), pairing system 700, any components included therein, and/or any implementation thereof.

In operation 1802, a pilot signal (e.g., pilot signal 1606-1) for an ultrasonic beacon transmission is detected. Operation 1802 may be performed in any suitable way, including any of the ways described herein. For example, the device may detect a sharp edge when first set 1612-1 switches to second set 1612-2.

In operation 1804, based on detection of the pilot signal, permutation information encoded in the pilot signal is extracted from the pilot signal. Operation 1804 may be performed in any suitable way, including any of the ways described herein. For example, in response to detecting the pilot signal, the pilot signal may be decoded and the permutation information may be stored as first transmission data in a temporary memory (e.g., a buffer or cache). Additionally or alternatively, raw (e.g., unprocessed) audio signal data generated based on the pilot signal may be stored in the temporary memory with the first transmission data.

In operation 1806, based on detection of the pilot signal, message information encoded in a message signal (e.g., pilot signal 1608-1) of the ultrasonic beacon is extracted from the message signal. Operation 1806 may be performed in any suitable way, including any of the ways described herein. For example, the transmission data stored in the temporary memory is updated to include the message subparts along with information indicating the subchannel on which each message subpart was transmitted.

In operation 1808, the message information may be validated. Operation 1808 may be performed in any suitable way, including any of the ways described herein. In some examples in which the message information includes validation information, a parity check, forward error correction, and/or any other suitable error detection procedure may be performed based on the validation information. In additional or alternative examples, the message information is validated based on identification information included in the message information that was extracted from the message signal and stored as the transmission data. The identification information extracted from the message signal may be compared with a database of identification information (e.g., association table 900). The database of identification information may be stored locally on the device or remotely on a remote computing system (e.g., computing system 802). If the identification information extracted from the message signal corresponds to known identification information (e.g., a location ID, a medical system ID, a beacon generator ID, a surgical session ID, etc.), then it is determined that the message information is valid. If the identification information extracted from the message signal does not correspond to any known identification information, then it is determined that the message information is not valid. In some examples, message information is valid only if both the validation information and the identification information encoded in the message signal are determined to be valid.

If the message information is determined to be valid, method 1800 proceeds to operation 1810. In operation 1810, in response to a determination that the message information is valid, an operation associated with a medical system associated with the ultrasonic beacon is performed. Operation 1810 may be performed in any suitable way, including any of the ways described herein. For example, a user device that detects the ultrasonic beacon may be communicatively paired with a medical system associated with the ultrasonic beacon (e.g., a medical system identified by, or associated with, the identification information encoded in the message signal).

If, on the other hand, the message information is determined to not be valid, method 1800 proceeds to operation 1812. In operation 1812, the message information is reconstructed from multiple different transmissions of the ultrasonic beacon. Operation 1812 may be performed in any suitable way.

For example, in response to a determination that the message information is not valid, the device may combine message subparts from different transmissions that were received on good quality subchannels. To this end, the device may be configured to determine the quality of the subchannels. The device may determine the subchannel quality in any suitable way. In some examples, the subchannel quality is determined based on the pilot signal. For example, as shown in FIG. 16, for each transmission 1604, the pilot signal 1606 on each subchannel 1610 has an ON signal and an OFF signal. Any audio signal detected by the device during transmission of an OFF signal is background noise. Accordingly, the device may determine a signal-to-noise ratio (SNR) based on the ON and OFF signals of the pilot signal 1606. Additionally or alternatively, the device may determine the SNR based on the OFF signal of the pilot signal 1606 and the message subpart subsequently transmitted on the same subchannel. In some examples, the SNR for each subchannel 1610 for each transmission 1604 may be determined when the pilot signal is detected, and the SNR information for each subchannel may be stored with the permutation information in the transmission data.

In some examples, only two transmissions 1604 may be used to reconstruct the message information. As shown in FIG. 16, the message information may be reconstructed using transmission 1604-2 and transmission 1604-1 (a prior transmission having a different permutation). In such examples, the subchannels selected for reconstructing the message information may be selected based on the SNR information stored in the transmission data. For example, SNR information for subchannels 1610-1 to 1610-4 may be lower than SNR information for subchannels 1610-5 to 1610-8. Accordingly, the message information may be reconstructed by combining the message subparts transmitted on subchannels 1610-5 to 1610-8. The permutation information stored in the transmission data may be used to reconstruct the message subparts in the correct sequence. Additionally or alternatively to using SNR to determine subchannel quality, signal strength may be detected and used to determine subchannel quality.

In other examples, more than two transmissions 1604 may be used to reconstruct the message information. As shown in FIG. 17, the message information may be reconstructed using four transmissions 1604-1 to 1604-4. In such examples, the subchannels selected for reconstructing the message information may be selected based on the subchannel having the best SNR, or based on weighting or averaging the SNR information for each subchannel. Subchannels may be weighted or averaged in any suitable way and by any suitable algorithm. For example, weighted or averaged SNR information for subchannels 1610-1 to 1610-4 may be lower than weighted or averaged SNR information for subchannels 1610-5 to 1610-8. Accordingly, the message information may be reconstructed by combining the message subparts transmitted on subchannels 1610-5 to 1610-8. The permutation information stored in the transmission data may be used to reconstruct the message subparts in the correct sequence.

After reconstructing the message information, method 1800 proceeds to operation 1814. In operation 1814, it is determined whether the reconstructed message is valid. Operation 1814 may be performed in any suitable way, including any of the ways described herein (e.g., in the same manner as explained for operation 1808).

If the reconstructed message information is determined to be valid, method 1800 proceeds to operation 1810. On the other hand, if the reconstructed message information is determined to not be valid, method 1800 returns to operation 1802 and awaits detection of the next ultrasonic beacon.

Performing subchannel cycling has several benefits. For example, subchannel cycling provides signal redundancy in case of subchannel dropout or corruption without requiring additional bandwidth or additional time when acoustic conditions are good. As a result, a device may be communicatively paired with a medical system quickly in good conditions. When some subchannels dropout or the signals are corrupt (e.g., due to heavy interference), the message can still be decoded using the combined information from two or more ultrasonic beacon transmissions. Accordingly, a user device may be communicatively paired with a medical system even in noisy acoustic environments or when the microphone on the user device is covered (e.g., when the user device is in a user's pocket).

In some situations, a multi-channel communication scheme may also be susceptible to high peak-to-average power ratio (PAPR). In conventional multi-channel communication schemes, PARR is reduced by optimizing the phase of blocks of subchannels and transmitting phase information to the receiver in a side channel. The optimal phase for each subchannel is determined based on probabilistic algorithms, traditional selective mapping (SLM), or partial transmit sequence (PTS) approaches, thereby consuming processing power. However, these conventional PAPR reduction techniques consume extra bandwidth. In an acoustic multi-channel communication scheme as described above, reducing bandwidth for message information requires increasing the duration of each ultrasonic beacon transmission and, hence, increasing the time it takes to pair a user device with a medical system.

To address these problems, an optimal phase may be assigned to each subchannel based on the message information. Because the message information generally does not change (e.g., transmissions 1604 are repeated indefinitely until terminated), the optimal phase for each subchannel (e.g., each subchannel 1610) may be easily predetermined (e.g., need not be determined for each transmission of the ultrasonic beacon). As a result, the optimal phase generally does not change, and the optimal phase information need not be transmitted to the receiving device when the multi-channel communication scheme uses OOK. Accordingly, PAPR may be reduced without reducing bandwidth for transmitting message information and without increasing pairing time for the receiving device. In some examples, the optimal phase for each subchannel may be determined in real-time (e.g., for each transmission of an ultrasonic beacon) due to the generally slow nature of ultrasound communications, but the optimal phase information need not be transmitted when the multi-channel communication scheme uses OOK.

The foregoing configurations and embodiments have focused on ultrasonic beacon-based systems. However, the present disclosure is not limited to these configurations and embodiments, as various modifications and changes may be made thereto without departing from the scope of the inventive principles described herein. For example, the systems and methods described herein may be based additionally or alternatively on any other suitable beacon or other push notifications, such as electromagnetic signals (e.g., infrared, radio-frequency identification (RFID), etc.), wireless data signals (e.g., Bluetooth, near-field communication, Wi-Fi, etc.), offline data transfer, and the like. Additionally or alternatively, the systems and methods described herein may be used in facilities and environments other than a medical facility, such as recreational facilities (e.g., amusement parks, sports stadiums, parks, etc.), educational facilities (e.g., schools, universities, etc.), shopping centers, business facilities (e.g., offices, research parks, etc.), laboratories, manufacturing facilities, transportation facilities (e.g., airports, train stations, etc.), and the like.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 19:
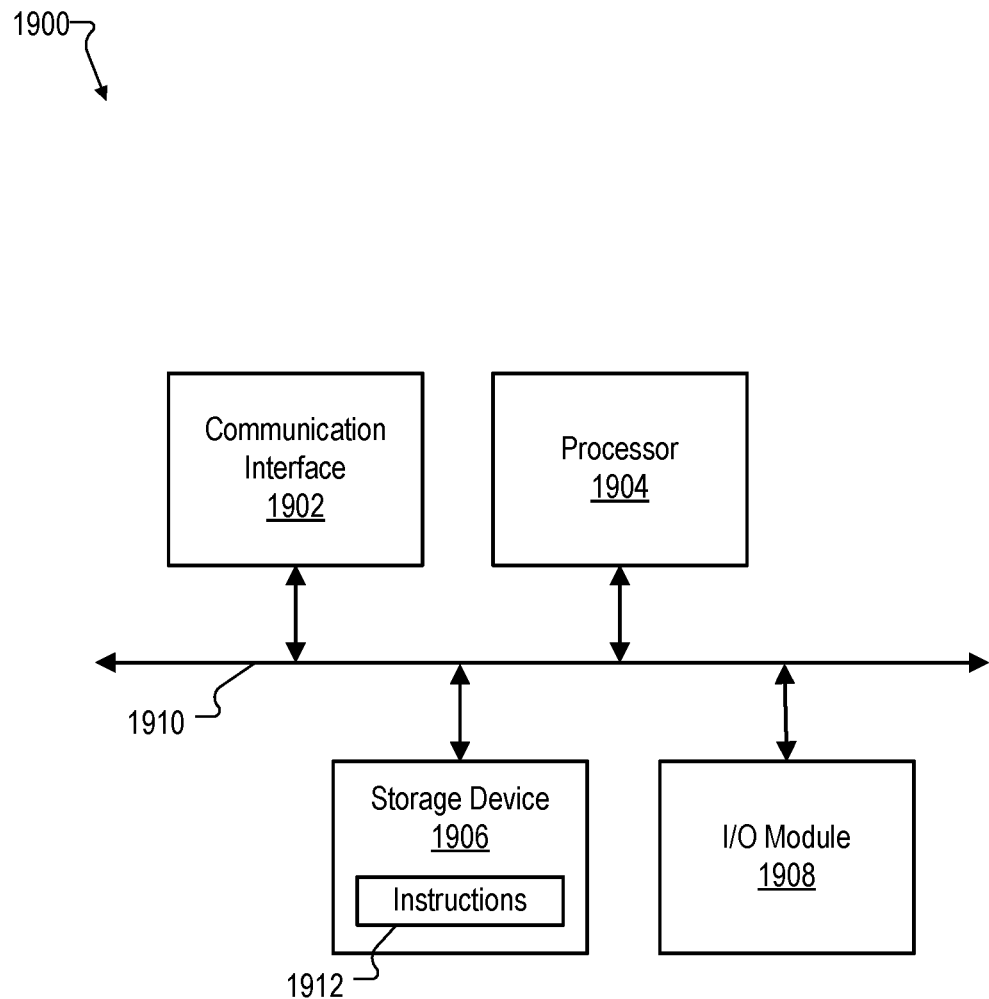
FIG. 19 illustrates an exemplary computing device according to principles described herein.

FIG. 19 illustrates an exemplary computing device 1900 that may be specifically configured to perform one or more of the processes described herein. Any of the systems, units, computing devices, and/or other components described herein may be implemented by computing device 1900.

As shown in FIG. 19, computing device 1900 may include a communication interface 1902, a processor 1904, a storage device 1906, and an input/output ("I/O") module 1908 communicatively connected one to another via a communication infrastructure 1910. While an exemplary computing device 1900 is shown in FIG. 19, the components illustrated in FIG. 19 are not intended to be limiting. Additional or alternative components may be used in other embodiments. Components of computing device 1900 shown in FIG. 19 will now be described in additional detail.

Communication interface 1902 may be configured to communicate with one or more computing devices. Examples of communication interface 1902 include, without limitation, a wired network interface (such as a network interface card), a wireless network interface (such as a wireless network interface card), a modem, an audio/video connection, and any other suitable interface.

Processor 1904 generally represents any type or form of processing unit capable of processing data and/or interpreting, executing, and/or directing execution of one or more of the instructions, processes, and/or operations described herein. Processor 1904 may perform operations by executing computer-executable instructions 1912 (e.g., an application, software, code, and/or other executable data instance) stored in storage device 1906.

Storage device 1906 may include one or more data storage media, devices, or configurations and may employ any type, form, and combination of data storage media and/or device. For example, storage device 1906 may include, but is not limited to, any combination of the non-volatile media and/or volatile media described herein. Electronic data, including data described herein, may be temporarily and/or permanently stored in storage device 1906. For example, data representative of computer-executable instructions 1912 configured to direct processor 1904 to perform any of the operations described herein may be stored within storage device 1906. In some examples, data may be arranged in one or more databases residing within storage device 1906.

I/O module 1908 may include one or more I/O modules configured to receive user input and provide user output. I/O module 1908 may include any hardware, firmware, software, or combination thereof supportive of input and output capabilities. For example, I/O module 1908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1908 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. An auxiliary device comprising:
   a sensor configured to detect a first set of ultrasonic beacons including identification information associated with a robotic surgical system that is different from the auxiliary device; and a processor configured to:
upon detection of the first set of ultrasonic beacons by the sensor of the auxiliary device, identify, based on the identification information included in the first set of ultrasonic beacons detected by the sensor of the auxiliary device, the robotic surgical system associated with the identification information included in the first set of ultrasonic beacons; and
communicatively pair the auxiliary device with the robotic surgical system associated with the identification information included in the first set of ultrasonic beacons.

2. The auxiliary device of claim 1, wherein:
the processor is further configured to determine that the first set of ultrasonic beacons includes all ultrasonic beacons associated with the robotic surgical system; and
the communicatively pairing of the auxiliary device with the robotic surgical system associated with the first set of ultrasonic beacons is performed based on the determination that the first set of ultrasonic beacons includes all ultrasonic beacons associated with the robotic surgical system.

3. The auxiliary device of claim 2, wherein the first set of ultrasonic beacons includes a unique component identifier for each component included in a plurality of components of the robotic surgical system.

4. The auxiliary device of claim 1, wherein:
the first set of ultrasonic beacons are emitted by a first set of ultrasonic beacon generators located within a first area, the first area including the robotic surgical system associated with the first set of ultrasonic beacons;
the sensor is further configured to detect a second set of ultrasonic beacons emitted by a second set of ultrasonic beacon generators located within a second area;
the processor is further configured to determine, based on the first set of ultrasonic beacons and the second set of ultrasonic beacons, that the auxiliary device is located within the first area; and
the communicatively pairing of the auxiliary device with the robotic surgical system associated with the first set of ultrasonic beacons is performed based on the determination that the auxiliary device is located within the first area.

5. The auxiliary device of claim 1, wherein:
the sensor is further configured to detect a second set of ultrasonic beacons;
the processor is further configured to determine that the first set of ultrasonic beacons includes more ultrasonic beacons than the second set of ultrasonic beacons; and
the communicatively pairing of the auxiliary device with the robotic surgical system associated with the first set of ultrasonic beacons is performed based on the determination that the first set of ultrasonic beacons includes more ultrasonic beacons than the second set of ultrasonic beacons.

6. The auxiliary device of claim 1, wherein:
the processor is further configured to determine that a threshold number of ultrasonic beacons in the first set of ultrasonic beacons, as detected by the sensor, has a signal strength greater than a threshold signal strength level; and
the communicatively pairing of the auxiliary device with the robotic surgical system associated with the first set of ultrasonic beacons is performed based on the determination that the threshold number of ultrasonic beacons in the first set of ultrasonic beacons, as detected by the sensor, has the signal strength greater than the threshold signal strength level.

7. The auxiliary device of claim 1, wherein:
the processor is further configured to determine that the sensor does not detect any ultrasonic beacons associated with another robotic surgical system; and
the communicatively pairing of the auxiliary device with the robotic surgical system associated with the first set of ultrasonic beacons is performed based on the determination that the sensor does not detect any ultrasonic beacons associated with another robotic surgical system.

8. The auxiliary device of claim 1, wherein:
the first set of ultrasonic beacons comprises a primary beacon and one or more secondary beacons;
the processor is further configured to determine that identification information included in the one or more secondary beacons matches identification information included in the primary beacon; and
the communicatively pairing of the auxiliary device with the robotic surgical system associated with the first set of ultrasonic beacons is performed based on the determination that the identification information included in the one or more secondary beacons matches the identification information included in the primary beacon.

9. The auxiliary device of claim 8, wherein:
the primary beacon includes identification information identifying each of a plurality of components of the robotic surgical system; and
each secondary beacon of the one or more secondary beacons includes identification information identifying a unique one of the plurality of components of the robotic surgical system.

10. A method comprising:
detecting, by a sensor included in an auxiliary device, a first set of ultrasonic beacons including identification information associated with a robotic surgical system that is different from the auxiliary device;
upon detecting the first set of ultrasonic beacons by the sensor of the auxiliary device, identifying, based on the identification information included in the first set of ultrasonic beacons, a medical system the robotic surgical system associated with the identification information included in the first set of ultrasonic beacons; and
communicatively pairing the auxiliary device with the robotic surgical system associated with the identification information included in the first set of ultrasonic beacons.

11. The method of claim 10, further comprising determining that the first set of ultrasonic beacons includes all ultrasonic beacons associated with the robotic surgical system;
wherein the communicatively pairing of the auxiliary device with the robotic surgical system associated with the first set of ultrasonic beacons is performed based on the determining that the first set of ultrasonic beacons includes all ultrasonic beacons associated with the robotic surgical system.

12. The method of claim 11, wherein the first set of ultrasonic beacons includes a unique component identifier for each component included in a plurality of components of the robotic surgical system.

13. The method of claim 10, wherein:
the first set of ultrasonic beacons are emitted by a first set of ultrasonic beacon generators located within a first area, the first area including the robotic surgical system associated with the first set of ultrasonic beacons;

the method further comprises:
- detecting, by the sensor, a second set of ultrasonic beacons emitted by a second set of ultrasonic beacon generators located within a second area; and
- determining, based on the first set of ultrasonic beacons and the second set of ultrasonic beacons, that the auxiliary device is located within the first area; and the communicatively pairing of the auxiliary device with the robotic surgical system associated with the first set of ultrasonic beacons is performed based on the determining that the auxiliary device is located within the first area.

14. The method of claim 10, further comprising:
- detecting, by the sensor, a second set of ultrasonic beacons; and
- determining that the first set of ultrasonic beacons includes more ultrasonic beacons than the second set of ultrasonic beacons;
- wherein the communicatively pairing of the auxiliary device with the robotic surgical system associated with the first set of ultrasonic beacons is performed based on the determining that the first set of ultrasonic beacons includes more ultrasonic beacons than the second set of ultrasonic beacons.

15. The method of claim 10, further comprising determining that a threshold number of ultrasonic beacons in the first set of ultrasonic beacons, as detected by the sensor, has a signal strength greater than a threshold signal strength level;
- wherein the communicatively pairing of the auxiliary device with the robotic surgical system associated with the first set of ultrasonic beacons is performed based on the determining that the threshold number of ultrasonic beacons in the first set of ultrasonic beacons, as detected by the sensor, has the signal strength greater than the threshold signal strength level.

16. The method of claim 10, further comprising determining that the sensor does not detect any ultrasonic beacons associated with another robotic surgical system;
- wherein the communicatively pairing of the auxiliary device with the robotic surgical system associated with the first set of ultrasonic beacons is performed based on the determining that the sensor does not detect any ultrasonic beacons associated with another robotic surgical system.

17. The method of claim 10, wherein:
the first set of ultrasonic beacons comprises a primary beacon and one or more secondary beacons;
the method further comprises determining that identification information included in the one or more secondary beacons matches identification information included in the primary beacon; and
the communicatively pairing of the auxiliary device with the robotic surgical system associated with the first set of ultrasonic beacons is performed based on the determining that the identification information included in the one or more secondary beacons matches the identification information included in the primary beacon.

18. The method of claim 17, wherein:
the primary beacon includes identification information identifying a plurality of components of the robotic surgical system; and
each secondary beacon of the one or more secondary beacons includes identification information identifying a unique one of the plurality of components of the robotic surgical system.

19. A system comprising:
a memory storing instructions; and
a processor communicatively coupled to the memory and configured to execute the instructions to:
- determine that an auxiliary device detects a first set of ultrasonic beacons including identification information associated with a robotic surgical system that is different from the auxiliary device, the first set of ultrasonic beacons being emitted by one or more ultrasonic beacon generators located at a first area of a medical facility;
- upon detection of the first set of ultrasonic beacons by a sensor of the auxiliary device, determine, based on the identification information included in the first set of ultrasonic beacons detected by the sensor of the auxiliary device, that the auxiliary device is located at the first area of the medical facility; and
- communicatively pair, based on the determining that the auxiliary device is located at the first area of the medical facility, the auxiliary device with a medical system the robotic surgical system located at the first area of the medical facility.

20. The system of claim 19, wherein:
the processor is further configured to execute the instructions to determine that the auxiliary device detects a second set of ultrasonic beacons, the second set of ultrasonic beacons being emitted by one or more ultrasonic beacon generators located at a second area of the medical facility; and
the determining that the auxiliary device is located at the first area of the medical facility is further based on the second set of ultrasonic beacons.

* * * * *

UNITED STATES PATENT AND TRADEMARK OFFICE
CERTIFICATE OF CORRECTION

PATENT NO. : 12,354,739 B2
APPLICATION NO. : 17/777520
DATED : July 8, 2025
INVENTOR(S) : Boris Foelsch et al.

It is certified that error appears in the above-identified patent and that said Letters Patent is hereby corrected as shown below:

In the Claims

Column 38, Claim 10, Line 42, delete "a medical system".

Column 40, Claim 19, Lines 36 to 37, delete "a medical system".

Signed and Sealed this
Twelfth Day of August, 2025

Coke Morgan Stewart
*Acting Director of the United States Patent and Trademark Office*